(12) United States Patent
Ogasawara et al.

(10) Patent No.: US 7,955,809 B2
(45) Date of Patent: Jun. 7, 2011

(54) METHOD FOR MEASURING HUMAN MEGALIN

(75) Inventors: Shinya Ogasawara, Niigata (JP); Shuhei Miura, Niigata (JP); Akihiko Saito, Niigata (JP); Tetsuro Takeda, Niigata (JP)

(73) Assignees: Niigata University, Niigata (JP); Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 12/293,992

(22) PCT Filed: Mar. 28, 2007

(86) PCT No.: PCT/JP2007/056660
§ 371 (c)(1),
(2), (4) Date: Sep. 22, 2008

(87) PCT Pub. No.: WO2007/119563
PCT Pub. Date: Oct. 25, 2007

(65) Prior Publication Data
US 2009/0117594 A1    May 7, 2009

(30) Foreign Application Priority Data

Mar. 28, 2006    (JP) ................. 2006-089306

(51) Int. Cl.
*G01N 33/53*    (2006.01)
(52) U.S. Cl. ........................... 435/7.1; 435/7.2; 436/518
(58) Field of Classification Search .................. None
See application file for complete search history.

(56) References Cited

U.S. PATENT DOCUMENTS

2004/0204357 A1    10/2004    Brautigam et al.
2004/0235161 A1*   11/2004    Tabata et al. .................. 435/371

FOREIGN PATENT DOCUMENTS

| JP | 4-351962 | 12/1992 |
| JP | 8-105889 | 4/1996 |
| WO | WO 03/102493 A1 | 12/2003 |

OTHER PUBLICATIONS

Jordan (The Protein Protocol Handbook, second edition, edited by Walker, year 2000, p. 1083-1088).*
Willnow et al. (PNAS 1996 vol. 93 p. 8460-8464).*
Marion De Jong PhD et al., "Megalin Is Essential for Renal Proximal Tubule Reabsorption of $^{111}$In-DTPA-Octreotide", The Journal of Nuclear Medicine, vol. 46, No. 10, Oct. 2005, pp. 1696-1700.
Supplementary European Search Report EP 07 74 0098 dated Aug. 24, 2009.
Arvi-Matti Kuusniemi et al., "Kidneys with heavy proteinuria show fibrosis, inflammation, and oxidative stress, but no tubular phenotypic change", Kidney International, vol. 68, (2005) pp. 121-132.
Anthony G. W. Norden et al., "Urinary Megalin Deficiency Implicates Abnormal Tubular Endocytic Function in Fanconi Syndrome", J. Am. Soc. Nephrol. 13: 125-133, 2002.
K. Kobayashi et al., "Conditions for Solubilization of Tamm-Horsfall Protein/Uromodulin In Human Urine and Establishment of a Sensitive and Accurate Enzyme-Linked Immunosorbent Assay (ELISA) Method", Archives of Biochemistry and Biophysics, vol. 388, No. 1, Apr. 1, 2001, pp. 113-120.
C.J. Ilsa Raats et al., "Reduction in Glomerular Heparan Sulfate Correlates with Complement Deposition and Albuminuria in Active Heymann Nephritis", J. Am. Soc. Nephrol. 10: 1689-1699, 1999.

* cited by examiner

*Primary Examiner* — Jacob Cheu
(74) *Attorney, Agent, or Firm* — Stephen A. Bent; Foley & Lardner LLP

(57) ABSTRACT

This invention provides a method for measuring human megalin that can be performed in a simpler manner within a shorter period of time than is possible with conventional techniques, and that can also quantify human megalin. This invention also provides a method that enables diagnosis of functional diseases, which are specific to cells, tissues, or organs, in a site-directed manner at an early stage. Measurement of human megalin enables detection of a disease in an organ in which megalin expression is observed.

11 Claims, 4 Drawing Sheets

SEQUENCE LISTING

<160> NUMBER OF SEQ ID NOS: 2

<210> SEQ ID NO 1
<211> LENGTH: 13968
<212> TYPE: DNA
<213> ORGANISM: Homo sapiens

<400> SEQUENCE: 1

```
atggatcgcg ggccggcagc agtggcgtgc acgctgctcc tggctctcgt cgcctgccta      60
gcgccggcca gtggccaaga atgtgacagt gcgcattttc gctgtggaag tgggcattgc     120
atccctgcag actggaggtg tgatgggacc aaagactgtt cagatgacgc ggatgaaatt     180
ggctgcgctg ttgtgaccct ccagcagggc tatttcaagt gccagagtga gggacaatgc     240
atccccagct cctgggtgtg tgaccaagat caagactgtg atgatggctc agatgaacgt     300
caagattgct cacaaagtac atgctcaagt catcagataa catgctccaa tggtcagtgt     360
atcccaagtg aatacaggtg cgaccacgtc agagactgcc ccgatggagc tgatgagaat     420
gactgccagt acccaacatg tgagcagctt acttgtgaca atgggcctg ctataacacc     480
agtcagaagt gtgattggaa agttgattgc agggactcct cagatgaaat caactgcact     540
gagatatgct tgcacaatga gttttcatgt ggcaatggag agtgtatccc tcgtgcttat     600
gtctgtgacc atgacaatga ttgccaagac ggcagtgatg aacatgcttg caactatccg     660
acctgcggtg gttaccagtt cacttgcccc agtggccgat gcatttatca aaactgggtt     720
tgtgatggag aagatgactg taaagataat ggagatgaag atggatgtga aagcggtcct     780
catgatgttc ataaatgttc cccaagagaa tggtcttgcc cagagtcggg acgatgcatc     840
tccatttata aagtttgtga tgggattttta gattgcccag aagagaaga tgaaaacaac     900
actagtaccg gaaaatactg tagtatgact ctgtgctctg ccttgaactg ccagtaccag     960
tgccatgaga cgccgtatgg aggagcgtgt ttttgtcccc caggttatat catcaaccac    1020
aatgacagcc gtacctgtgt tgagtttgat gattgccaga tatggggaat ttgtgaccag    1080
aagtgtgaaa gccgacctgg ccgtcacctg tgccactgtg aagaaggta tatcttggag    1140
cgtggacagt attgcaaagc taatgattcc tttggcgagg cctccattat cttctccaat    1200
ggtcgggatt tgttaattgg tgatattcat ggaaggagct tccggatcct agtggagtct    1260
cagaatcgtg gagtgccgt gggtgtggct ttccactatc acctgcaaag agttttttgg    1320
acagacaccg tgcaaaataa ggttttttca gttgacatta atggtttaaa tatccaagag    1380
gttctcaatg tttctgttga aaccccagag aacctggctg tggactgggt taataataaa    1440
```

```
atctatctag tggaaaccaa ggtcaaccgc atagatatgg taaatttgga tggaagctat    1500
cgggttaccc ttataactga aaacttgggg catcctagag gaattgccgt ggacccaact    1560
gttggttatt tattttttctc agattgggag agccttttctg gggaacctaa gctggaaagg   1620
gcattcatgg atggcagcaa ccgtaaagac ttggtgaaaa caaagctggg atggcctgct    1680
ggggtaactc tggatatgat atcgaagcgt gtttactggg ttgactctcg gtttgattac    1740
attgaaactg taacttatga tggaattcaa aggaagactg tagttcatgg aggctccctc    1800
attcctcatc cctttggagt aagcttattt gaaggtcagg tgttctttac agattggaca    1860
aagatggccg tgctgaaggc aaacaagttc acagagacca acccacaagt gtactaccag    1920
gcttccctga ggccctatgg agtgactgtt taccattccc tcagacagcc ctatgctacc    1980
aatccgtgta aagataacaa tgggggctgt gagcaggtct gtgttctcag ccacagaaca    2040
gataatgatg gtttgggttt ccgttgcaag tgcacattcg gcttccaact ggatacagat    2100
gagcgccact gcattgctgt tcagaatttc ctcattttttt catcccaagt tgctattcgt    2160
gggatcccgt tcaccttgtc tacccaggaa gatgtcatgg ttccagtttc ggggaatcct    2220
tctttctttg tcgggattga ttttgacgcc caggacagca ctatctttttt ttcagatatg    2280 tcaaaacaca tgattttttaa gcaaaagatt gatggcacag gaagagaaat tctcgcagct    2340
aacagggtgg aaaatgttga agtttggct ttttgattgga tttcaaagaa tctctattgg    2400
acagactctc attacaagag tatcagtgtc atgaggctag ctgataaaac gagacgcaca    2460
gtagttcagt atttaaataa cccacggtcg gtggtagttc atccttttgc cgggtatcta    2520
ttcttcactg attggttccg tcctgctaaa attatgagag catggagtga cggatctcac    2580
ctcttgcctt aataaacac tactcttgga tggcccaatg gcttggccat cgattgggct    2640
gcttcacgat tgtactgggt agatgcctat tttgataaaa ttgagcacag caccttttgat    2700 ggtttagaca gaagaagact gggccatata gagcagatga cacatccgtt tggacttgcc    2760
atctttggag agcatttatt ttttactgac tggagactgg gtgccattat tcgagtcagg    2820
aaagcagatg tgggagaaat gacagttatc gaagtggca ttgcttacat actgcatttg     2880
aaatcgtatg atgtcaacat ccagactggt tctaacgcct gtaatcaacc cacgcatcct    2940
aacggtgact gcagccactt ctgcttcccg gtgccaaatt ccagcgagt gtgtgggtgc     3000 ccttatggaa tgaggctggc ttccaatcac ttgacatgcg agggggaccc aaccaatgaa    3060
ccacccacgg agcagtgtgg cttatttttcc ttccctgta aaaatggcag atgtgtgccc     3120
aattactatc tctgtgatgg agtcgatgat tgtcatgata acagtgatga gcaactatgt    3180
ggcacactta ataatacctg ttcatcttcg gcgttcacct gtggccatgg ggagtgcatt    3240
cctgcacact ggcgctgtga caaacgcaac gactgtgtgg atggcagtga tgagcacaac    3300
tgccccaccc acgcacctgc ttcctgcctt gacacccaat acacctgtga taatcaccag    3360
tgtatctcaa agaactgggt ctgtgacaca gacaatgatt gtggggatgg atctgatgaa    3420
aagaactgca attcgacaga gacatgccaa cctagtcagt ttaattgccc caatcatcga    3480
tgtattgacc tatcgtttgt ctgtgatggt gacaaggatt gtgttgatgg atctgatgag    3540
gttggttgtg tattaaactg tactgcttct caattcaagt gtgccagtgg ggataaatgt    3600
attggcgtca caaatcgttg tgatggtgtt tttgattgca gtgacaactc ggatgaagcg    3660
ggctgtccaa ccaggcctcc tggtatgtgc cactcagatg aatttcagtg ccaagaagat    3720
ggtatctgca tcccgaactt ctgggaatgt gatgggcatc cagactgcct ctatggatct    3780
gatgagcaca atgcctgtgt ccccaagact tgcccttcat catatttcca ctgtgacaac    3840
```

```
ggaaactgca tccacagggc atggctctgt gatcgggaca atgactgcgg ggatatgagt   3900
gatgagaagg actgccctac tcagcccttt cgctgtccta gttggcaatg gcagtgtctt   3960
ggccataaca tctgtgtgaa tctgagtgta gtgtgtgatg catctttga ctgccccaat    4020
gggacagatg agtccccact ttgcaatggg aacagctgct cagatttcaa tggtggttgt   4080
actcacgagt gtgttcaaga gcccttrggg gctaaatgcc tatgtccatt gggattctta   4140
cttgccaatg attctaagac ctgtgaagac atagatgaat gtgatattct aggctcttgt   4200
agccagcact gttacaatat gagaggttct ttccggtgct cgtgtgatac aggctacatg   4260
ttagaaagtg atgggaggac ttgcaaagtt acagcatctg agagtctgct gttacttgtg   4320
gcaagtcaga acaaaattat tgccgacagt gtcacctccc aggtccacaa tatctattca   4380
ttggtcgaga atggttctta cattgtagct gttgattttg attcaattag tggtcgtatc   4440
ttttggtctg atgcaactca gggtaaaacc tggagtgcgt tcaaaatgg aacggacaga    4500
agagtggtat ttgacagtag catcatcttg actgaaacta ttgcaataga ttgggtaggt   4560
cgtaatcttt actggacaga ctatgctctg gaaacaattg aagtctccaa aattgatggg   4620
agccacagga ctgtgctgat tagtaaaaac ctaacaaatc caagaggact agcattagat   4680
cccagaatga atgagcatct actgttctgg tctgactggg ccaccaccc tcgcatcgag    4740
cgagccagca tggacggcag catgcgcact gtcattgtcc aggacaagat cttctggccc   4800
tgcggcttaa ctattgacta ccccaacaga ctgctctact tcatggactc ctatcttgat   4860
tacatggact tttgcgatta taatggacac catcggagac aggtgatagc cagtgatttg   4920
attatacggc accctatgc cctaactctc tttgaagact ctgtgtactg gactgaccgt    4980
gctactcgtc gggttatgcg agccaacaag tggcatggag ggaaccagtc agttgtaatg   5040
tataatattc aatggcccct tgggattgtt gcggttcatc cttcgaaaca accaaattcc   5100
gtgaatccat gtgccttttc ccgctgcagc catctctgcc tgctttcctc acagggtcct   5160
cattttact cctgtgtttg tccttcagga tggagtctgt ctcctgatct cctgaattgc    5220
ttgagagatg atcaaccttt cttaataact gtaaggcaac atataatttt tggaatctcc   5280
cttaatcctg aggtgaagag caatgatgct atggtcccca tagcagggat acagaatggt   5340
ttagatgttg aatttgatga tgctgagcaa tacatctatt gggttgaaaa tccaggtgaa   5400
attcacagag tgaagacaga tggcaccaac aggacagtat ttgcttctat atctatggtg   5460
gggccttcta tgaacctggc cttagattgg atttcaagaa acctttattc taccaatcct   5520
agaactcagt caatcgaggt tttgacactc cacggagata tcagatacag aaaaacattg   5580
attgccaatg atgggacagc tcttggagtt ggctttccaa ttggcataac tgttgatcct   5640
gctcgtggga agctgtactg gtcagaccaa ggaactgaca gtgggttcc tgccaagatc    5700
gccagtgcta acatgatgg cacatctgtg aaaactctct ttactgggaa cctcgaacac    5760
ctggagtgtg tcactcttga catcgaagag cagaaactct actgggcagt cactggaaga   5820
ggagtgattg aaagaggaaa cgtggatgga acagatcgga tgatcctggt acaccagctt   5880
tcccacccct ggggaattgc agtccatgat tctttccttt attatactga tgaacagtat   5940
gaggtcattg aaagagttga taaggccact ggggccaaca aaatagtctt gagagataat   6000
gttccaaatc tgaggggtct tcaagtttat cacagacgca atgccgccga atcctcaaat   6060
ggctgtagca acaacatgaa tgcctgtcag cagatttgcc tgcctgtacc aggaggattg   6120
ttttcctgcg cctgtgccac tggatttaaa ctcaatcctg ataatcggtc ctgctctcca   6180
tataactctt tcattgttgt ttcaatgctg tctgcaatca gaggctttag cttggaattg   6240
```

```
tcagatcatt cagaaaccat ggtgccggtg gcaggccaag gacgaaacgc actgcatgtg    6300
gatgtggatg tgtcctctgg ctttatttat tggtgtgatt ttagcagctc agtggcatct    6360
gataatgcga tccgtagaat taaaccagat ggatcttctc tgatgaacat tgtgacacat    6420
ggaataggag aaaatggagt ccggggtatt gcagtggatt gggtagcagg aaatctttat    6480
ttcaccaatg cctttgtttc tgaaacactg atagaagttc tgcggatcaa tactacttac    6540
cgccgtgttc ttcttaaagt cacagtggac atgcctaggc atattgttgt agatcccaag    6600
aacagatacc tcttctgggc tgactatggg cagagaccaa agattgagcg ttctttcctt    6660
gactgtacca atcgaacagt gcttgtgtca gagggcattg tcacaccacg gggcttggca    6720
gtggaccgaa gtgatggcta cgtttattgg gttgatgatt ctttagatat aattgcaagg    6780
attcgtatca atggagagaa ctctgaagtg attcgttatg cagtcgtta cccaactcct    6840 tatggcatca ctgtttttga aaattctatc atatgggtag ataggaattt gaaaaagatc    6900
ttccaagcca gcaaggaacc agagaacaca gagccaccca cagtgataag agacaatatc    6960
aactggctaa gagatgtgac catctttgac aagcaagtcc agccccggtc accagcagag    7020
gtcaacaaca cccttgcttg gaaaacaat ggtgggtgct ctcatctctg ctttgctctg    7080
cctggattgc acaccccaaa atgtgactgt gcctttggga ccctgcaaag tgatggcaag    7140
aattgtgcca tttcaacaga aaatttcctc atctttgcct tgtctaattc cttgagaagc    7200
ttacacttgg accctgaaaa ccatagccca cctttccaaa caataaatgt ggaaagaact    7260
gtcatgtctc tagactatga cagtgtaagt gatagaatct acttcacaca aaatttagcc    7320
tctggagttg gacagatttc ctatgccacc ctgtcttcag ggatccatac tccaactgtc    7380
attgcttcag gtataqggac tgctgatggc attgcctttg actggattac tagaagaatt    7440
tattacagtg actacctcaa ccagatgatt aattccatgg ctgaagatgg gtctaaccgc    7500
actgtgatag cccgcgttcc aaaaccaaga gcaattgtgt tagatccctg ccaagggtac    7560
ctgtactggg ctgactggga tacacatgcc aaaatcgaga gagccacatt gggaggaaac    7620
ttccgggtac ccattgtgaa cagcagtctg gtcatgccca gtgggctgac tctggactat    7680
gaagaggacc ttctctactg ggtggatgct agtctgcaga ggattgaacg cagcactctg    7740
acgggcgtgg atcgtgaagt cattgtcaat gcagccgttc atgcttttgg cttgactctc    7800
tatggccagt atatttactg gactgacttg tacacacaaa gaatttaccg agctaacaaa    7860
tatgacgggt caggtcagat tgcaatgacc acaaatttgc tctcccagcc caggggaatc    7920
aacactgttg tgaagaacca gaaacaacag tgtaacaatc cttgtgaaca gtttaatggg    7980
ggctgcagcc atatctgtgc accaggtcca aatggtgccg agtgccagtg tccacatgag    8040
ggcaactggt atttggccaa caacaggaag cactgcattg tggacaatgg tgaacgatgt    8100
ggtgcatctt ccttcacctg ctccaatggg cgctgcatct cggaagagtg gaagtgtgat    8160
aatgacaacg actgtgggga tggcagtgat gagatggaaa tgtctgtgc acttcacacc    8220 tgctcaccga cagccttcac ctgtgccaat gggcgatgtg tccaatactc ttaccgctgt    8280
gattactaca atgactgtgg tgatggcagt gatgaggcag ggtgcctgtt caaggactgc    8340
aatgccacca cggagtttat gtgcaataac agaaggtgca tacctcgtga gtttatctgc    8400
aatggtgtag acaactgcca tgataataac acttcagatg agaaaaattg ccctgatcgc    8460
acttgccagt ctggatacac aaaatgtcat aattcaaata tttgtattcc tcgcgtttat    8520
ttgtgtgacg gagacaatga ctgtggagat aacagtgatg aaaaccctac ttattgcacc    8580
actcacacat gcagcagcag tgagttccaa tgcgcatctg ggcgctgtat tcctcaacat    8640
```

```
tggtattgtg atcaagaaac agattgtttt gatgcctctg atgaacctgc ctcttgtggt    8700
cactctgagc gaacatgcct agctgatgag ttcaagtgtg atggtgggag gtgcatccca    8760
agcgaatgga tctgtgacgg tgataatgac tgtggggata tgagtgacga ggataaaagg    8820
caccagtgtc agaatcaaaa ctgctcggat tccgagtttc tctgtgtaaa tgacagacct    8880
ccggacagga ggtgcattcc ccagtcttgg gtctgtgatg cgatgtgga ttgtactgac     8940
ggctacgatg agaatcagaa ttgcaccagg agaacttgct ctgaaaatga attcacctgt    9000
ggttacggac tgtgtatccc aaagatattc aggtgtgacc ggcacaatga ctgtggtgac    9060
tatagcgacg agaggggctg cttataccag acttgccaac agaatcagtt tacctgtcag    9120
aacgggcgct gcattagtaa aaccttcgtc tgtgatgagg ataatgactg tggagacgga    9180
tctgatgagc tgatgcacct gtgccacacc ccagaaccca cgtgtccacc tcacgagttc    9240
aagtgtgaca tgggcgctg catcgagatg atgaaactct gcaaccacct agatgactgt    9300
ttggacaaca gcgatgagaa aggctgtggc attaatgaat gccatgaccc ttcaatcagt    9360
ggctgcgatc acaactgcac agacaccta accagtttct attgttcctg tcgtcctggt    9420
tacaagctca tgtctgacaa gcggacttgt gttgatattg atgaatgcac agagatgcct    9480
tttgtctgta gccagaagtg tgagaatgta ataggctcct acatctgtaa gtgtgcccca    9540
ggctacctcc gagaaccaga tggaaagacc tgccggcaaa acagtaacat cgaaccctat    9600
ctcattttta gcaaccgtta ctatttgaga aatttaacta tagatggcta ttttactcc    9660
ctcatcttgg aaggactgga caatgttgtg gcattagatt ttgaccgagt agagaagaga    9720
ttgtattgga ttgatacaca gaggcaagtc attgagagaa tgtttctgaa taagacaaac    9780
aaggagacaa tcataaacca cagactacca gctgcagaaa gtctggctgt agactgggtt    9840
tccagaaagc tctactggtt ggatgcccgc ctggatggcc tctttgtctc tgacctcaat    9900
ggtggacacc gccgcatgct ggcccagcac tgtgtggatg ccaacaacac cttctgcttt    9960
gataatccca gaggacttgc ccttcaccct caatatgggt acctctactg ggcagactgg   10020
ggtcaccgcg catacattgg gagagtaggc atggatggaa ccaacaagtc tgtgataatc   10080
tccaccaagt tagagtggcc taatggcatc accattgatt acaccaatga tctactctac   10140
tgggcagatg cccacctggg ttacatagag tactctgatt tggagggcca ccatcgacac   10200
acggtgtatg atgggcact gcctcaccct ttcgctatta ccattttga agacactatt   10260
tattggacag attggaatac aaggacagtg gaaaagggaa acaaatatga tggatcaaat   10320
agacagacac tggtgaacac aacacacaga ccatttgaca tccatgtgta ccatccatat   10380
aggcagccca ttgtgagcaa tcctgtggt accaacaatg gtggctgttc tcatctctgc   10440
ctcatcaagc caggaggaaa agggttcact tgcgagtgtc cagatgactt ccgcacccct   10500
caactgagtg gcagcaccta ctgcatgccc atgtgctcca gcacccagtt cctgtgcgct   10560
aacaatgaaa agtgcattcc tatctggtgg aaatgtgatg gacagaaaga ctgctcagat   10620
ggctctgatg aactggccct ttgcccgcag cgcttctgcc gactgggaca gttccagtgc   10680
agtgacggca actgcaccag cccgcagact ttatgcaatg ctcaccaaaa ttgccctgat   10740
gggtctgatg aagaccgtct tctttgtgag aatcaccact gtgactccaa tgaatggcag   10800
tgcgccaaca aacgttgcat cccagaatcc tggcagtgtg acacatttaa cgactgtgag   10860
gataactcag atgaagacag ttcccactgt gccagcagga cctgccggcc gggccagttt   10920
cggtgtgcta atggccgctg catcccgcag gcctggaagt gtgatgtgga taatgattgt   10980
ggagaccact cggatgagcc cattgaagaa tgcatgagct ctgcccatct ctgtgacaac   11040
```

```
ttcacagaat tcagctgcaa aacaaattac cgctgcatcc caaagtgggc cgtgtgcaat    11100
ggtgtagatg actgcaggga caacagtgat gagcaaggct gtgaggagag gacatgccat    11160 cctgtgggg atttccgctg taaaaatcac cactgcatcc ctcttcgttg gcagtgtgat    11220
gggcaaaatg actgtggaga taactcagat gaggaaaact gtgctccccg ggagtgcaca    11280
gagagcgagt ttcgatgtgt caatcagcag tgcattccct cgcgatggat ctgtgaccat    11340
tacaacgact gtggggacaa ctcagatgaa cgggactgtg agatgaggac ctgccatcct    11400
gaatattttc agtgtacaag tggacattgt gtacacagtg aactgaaatg cgatggatcc    11460
gctgactgtt tggatgcgtc tgatgaagct gattgtccca cacgctttcc tgatggtgca    11520
tactgccagg ctactatgtt cgaatgcaaa aaccatgttt gtatcccgcc atattggaaa    11580
tgtgatggcg atgatgactg tggcgatggt tcagatgaag aacttcacct gtgcttggat    11640
gttccctgta attcaccaaa ccgtttccgg tgtgacaaca atcgctgcat ttatagtcat    11700
gaggtgtgca atggtgtgga tgactgtgga gatggaactg atgagacaga ggagcactgt    11760
agaaaaccga cccctaaacc ttgtacagaa tatgaatata agtgtggcaa tgggcattgc    11820
attccacatg acaatgtgtg tgatgatgcc gatgactgtg tgactggtc cgatgaactg    11880 ggttgcaata aggaaaaga aagaacatgt gctgaaaata tatgcgagca aaattgtacc    11940
caattaaatg aaggaggatt tatctgctcc tgtacagctg ggttcgaaac caatgttttt    12000
gacagaacct cctgtctaga tatcaatgaa tgtgaacaat ttgggacttg tccccagcac    12060
tgcagaaata ccaaaggaag ttatgagtgt gtctgtgctg atggcttcac gtctatgagt    12120
gaccgccctg aaaacgatg tgcagctgag ggtagctctc ctttgttgct actgcctgac    12180
aatgtccgaa ttcgaaaata taatctctca tctgagaggt tctcagagta tcttcaagat    12240
gaggaatata tccaagctgt tgattatgat tgggatccca aggacatagg cctcagtgtt    12300
gtgtattaca ctgtgcgagg ggaggctct aggttggtg ctatcaaacg tgcctacatc    12360
cccaactttg aatccggccg caataatctt gtgcaggaag ttgacctgaa actgaaatac    12420
gtaatgcagc cagatggaat agcagtggac tgggttggaa ggcatattta ctggtcagat    12480
gtcaagaata aacgcattga ggtggctaaa cttgatggaa ggtacagaaa gtggctgatt    12540
tccactgacc tggaccaacc agctgctatt gctgtgaatc ccaaactagg gcttatgttc    12600
tggactgact ggggaaagga acctaaaatc gagtctgcct ggatgaatgg agaggaccgc    12660
aacatcctgg ttttcgagga ccttggttgg ccaactggcc tttctatcga ttattgaac    12720 aatgaccgaa tctactggag tgacttcaag gaggacgtta ttgaaaccat aaaatatgat    12780
gggactgata ggagagtcat tgcaaaggaa gcaatgaacc cttacagcct ggacatcttt    12840
gaagaccagt tatactggat atctaaggaa aagggagaag tatggaaaca aaataaattt    12900
gggcaaggaa agaaagagaa aacgctggta gtgaacccctt ggctcactca agttcgaatc    12960
tttcatcaac tcagatacaa taagtcagtg cccaaccttt gcaaacagat ctgcagccac    13020
ctctgccttc tgagacctgg aggatacagc tgtgcctgtc cccaaggctc cagctttata    13080
gaggggagca ccactgagtg tgatgcagcc atcgaactgc ctatcaacct gccccccca    13140 tgcaggtgca tgcacggagg aaattgctat tttgatgaga ctgacctccc caaatgcaag    13200
tgtcctagcg gctacaccgg aaaatattgt gaaatgcgct tttcaaaagg catctctcca    13260
ggaacaaccg cagtagctgt gctgttgaca atcctcttga tcgtcgtaat tggagctctg    13320
gcaattgcag gattcttcca ctatagaagg accggctccc ttttgcctgc tctgcccaag    13380
ctgccaagct taagcagtct cgtcaagccc tctgaaaatg ggaatggggt gaccttcaga    13440
```

```
tcaggggcag atcttaacat ggatattgga gtgtctggtt ttggacctga gactgctatt    13500
gacaggtcaa tggcaatgag tgaagacttt gtcatggaaa tggggaagca gcccataata    13560
tttgaaaacc caatgtactc agccagagac agtgctgtca aagtggttca gccaatccag    13620
gtgactgtat ctgaaaatgt ggataataag aattatggaa gtcccataaa cccttctgag    13680
atagttccag agacaaaccc aacttcacca gctgctgatg gaactcaggt gacaaaatgg    13740
aatctcttca acgaaaatc taaacaaact accaactttg aaaatccaat ctatgcacag    13800
atggagaacg agcaaaagga agtgttgct gcgacaccac ctccatcacc ttcgctccct    13860
gctaagccta agcctccttc gagaagagac ccaactccaa cctattctgc aacagaagac    13920
acttttaaag acaccgcaaa tcttgttaaa gaagactctg aagtatag                13968
```

<210> SEQ ID NO 2
<211> LENGTH: 4655
<212> TYPE: PRT
<213> ORGANISM: Homo sapiens

<400> SEQUENCE: 2

```
Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
        35                  40                  45

Gly Thr Lys Asp Cys Ser Asp Asp Ala Asp Glu Ile Gly Cys Ala Val
    50                  55                  60

Val Thr Cys Gln Gln Gly Tyr Phe Lys Cys Gln Ser Glu Gly Gln Cys
65                  70                  75                  80

Ile Pro Ser Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
        115                 120                 125

His Val Arg Asp Cys Pro Asp Gly Ala Asp Glu Asn Asp Cys Gln Tyr
    130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
                180                 185                 190

Gly Glu Cys Ile Pro Arg Ala Tyr Val Cys Asp His Asp Asn Asp Cys
        195                 200                 205

Gln Asp Gly Ser Asp Glu His Ala Cys Asn Tyr Pro Thr Cys Gly Gly
    210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
        275                 280                 285
```

```
Ile Leu Asp Cys Pro Gly Arg Glu Asp Glu Asn Asn Thr Ser Thr Gly
    290                 295                 300
Lys Tyr Cys Ser Met Thr Leu Cys Ser Ala Leu Asn Cys Gln Tyr Gln
305                 310                 315                 320
Cys His Glu Thr Pro Tyr Gly Gly Ala Cys Phe Cys Pro Pro Gly Tyr
                325                 330                 335
Ile Ile Asn His Asn Asp Ser Arg Thr Cys Val Glu Phe Asp Asp Cys
            340                 345                 350
Gln Ile Trp Gly Ile Cys Asp Gln Lys Cys Glu Ser Arg Pro Gly Arg
        355                 360                 365
His Leu Cys His Cys Glu Glu Gly Tyr Ile Leu Glu Arg Gly Gln Tyr
    370                 375                 380
Cys Lys Ala Asn Asp Ser Phe Gly Glu Ala Ser Ile Ile Phe Ser Asn
385                 390                 395                 400
Gly Arg Asp Leu Leu Ile Gly Asp Ile His Gly Arg Ser Phe Arg Ile
                405                 410                 415
Leu Val Glu Ser Gln Asn Arg Gly Val Ala Val Gly Val Ala Phe His
            420                 425                 430
Tyr His Leu Gln Arg Val Phe Trp Thr Asp Thr Val Gln Asn Lys Val
        435                 440                 445
Phe Ser Val Asp Ile Asn Gly Leu Asn Ile Gln Glu Val Leu Asn Val
    450                 455                 460
Ser Val Glu Thr Pro Glu Asn Leu Ala Val Asp Trp Val Asn Asn Lys
465                 470                 475                 480
Ile Tyr Leu Val Glu Thr Lys Val Asn Arg Ile Asp Met Val Asn Leu
                485                 490                 495
Asp Gly Ser Tyr Arg Val Thr Leu Ile Thr Glu Asn Leu Gly His Pro
            500                 505                 510
Arg Gly Ile Ala Val Asp Pro Thr Val Gly Tyr Leu Phe Phe Ser Asp
        515                 520                 525
Trp Glu Ser Leu Ser Gly Glu Pro Lys Leu Glu Arg Ala Phe Met Asp
    530                 535                 540
Gly Ser Asn Arg Lys Asp Leu Val Lys Thr Lys Leu Gly Trp Pro Ala
545                 550                 555                 560
Gly Val Thr Leu Asp Met Ile Ser Lys Arg Val Tyr Trp Val Asp Ser
                565                 570                 575
Arg Phe Asp Tyr Ile Glu Thr Val Thr Tyr Asp Gly Ile Gln Arg Lys
            580                 585                 590
Thr Val Val His Gly Gly Ser Leu Ile Pro His Pro Phe Gly Val Ser
        595                 600                 605
Leu Phe Glu Gly Gln Val Phe Phe Thr Asp Trp Thr Lys Met Ala Val
    610                 615                 620
Leu Lys Ala Asn Lys Phe Thr Glu Thr Asn Pro Gln Val Tyr Tyr Gln
625                 630                 635                 640
Ala Ser Leu Arg Pro Tyr Gly Val Thr Val Tyr His Ser Leu Arg Gln
                645                 650                 655
Pro Tyr Ala Thr Asn Pro Cys Lys Asp Asn Asn Gly Gly Cys Glu Gln
            660                 665                 670
Val Cys Val Leu Ser His Arg Thr Asp Asn Asp Gly Leu Gly Phe Arg
        675                 680                 685
Cys Lys Cys Thr Phe Gly Phe Gln Leu Asp Thr Asp Glu Arg His Cys
    690                 695                 700
Ile Ala Val Gln Asn Phe Leu Ile Phe Ser Ser Gln Val Ala Ile Arg
```

```
                705                 710                 715                 720
Gly Ile Pro Phe Thr Leu Ser Thr Gln Glu Asp Val Met Val Pro Val
                    725                 730                 735

Ser Gly Asn Pro Ser Phe Phe Val Gly Ile Asp Phe Asp Ala Gln Asp
                740                 745                 750

Ser Thr Ile Phe Phe Ser Asp Met Ser Lys His Met Ile Phe Lys Gln
            755                 760                 765

Lys Ile Asp Gly Thr Gly Arg Glu Ile Leu Ala Ala Asn Arg Val Glu
        770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
                820                 825                 830

Val His Pro Phe Ala Gly Tyr Leu Phe Phe Thr Asp Trp Phe Arg Pro
                835                 840                 845

Ala Lys Ile Met Arg Ala Trp Ser Asp Gly Ser His Leu Leu Pro Val
            850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Arg Leu Gly His Ile Glu Gln
                900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
        930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
                980                 985                 990

Asn Phe Gln Arg Val Cys Gly Cys Pro Tyr Gly Met Arg Leu Ala Ser
            995                 1000                1005

Asn His Leu Thr Cys Glu Gly Asp Pro Thr Asn Glu Pro Pro Thr Glu
        1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
                1045                1050                1055

Glu Gln Leu Cys Gly Thr Leu Asn Asn Thr Cys Ser Ser Ser Ala Phe
                1060                1065                1070

Thr Cys Gly His Gly Glu Cys Ile Pro Ala His Trp Arg Cys Asp Lys
            1075                1080                1085

Arg Asn Asp Cys Val Asp Gly Ser Asp Glu His Asn Cys Pro Thr His
        1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
                1125                1130                1135
```

-continued

```
Gly Ser Asp Glu Lys Asn Cys Asn Ser Thr Glu Thr Cys Gln Pro Ser
            1140                1145                1150

Gln Phe Asn Cys Pro Asn His Arg Cys Ile Asp Leu Ser Phe Val Cys
    1155                1160                1165

Asp Gly Asp Lys Asp Cys Val Asp Gly Ser Asp Glu Val Gly Cys Val
    1170                1175                1180

Leu Asn Cys Thr Ala Ser Gln Phe Lys Cys Ala Ser Gly Asp Lys Cys
1185                1190                1195                1200

Ile Gly Val Thr Asn Arg Cys Asp Gly Val Phe Asp Cys Ser Asp Asn
        1205                1210                1215

Ser Asp Glu Ala Gly Cys Pro Thr Arg Pro Pro Gly Met Cys His Ser
            1220                1225                1230

Asp Glu Phe Gln Cys Gln Glu Asp Gly Ile Cys Ile Pro Asn Phe Trp
    1235                1240                1245

Glu Cys Asp Gly His Pro Asp Cys Leu Tyr Gly Ser Asp Glu His Asn
    1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
        1285                1290                1295

Gly Asp Met Ser Asp Glu Lys Asp Cys Pro Thr Gln Pro Phe Arg Cys
            1300                1305                1310

Pro Ser Trp Gln Trp Gln Cys Leu Gly His Asn Ile Cys Val Asn Leu
    1315                1320                1325

Ser Val Val Cys Asp Gly Ile Phe Asp Cys Pro Asn Gly Thr Asp Glu
    1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
        1365                1370                1375

Leu Gly Phe Leu Leu Ala Asn Asp Ser Lys Thr Cys Glu Asp Ile Asp
    1380                1385                1390

Glu Cys Asp Ile Leu Gly Ser Cys Ser Gln His Cys Tyr Asn Met Arg
    1395                1400                1405

Gly Ser Phe Arg Cys Ser Cys Asp Thr Gly Tyr Met Leu Glu Ser Asp
    1410                1415                1420

Gly Arg Thr Cys Lys Val Thr Ala Ser Glu Ser Leu Leu Leu Leu Val
1425                1430                1435                1440

Ala Ser Gln Asn Lys Ile Ile Ala Asp Ser Val Thr Ser Gln Val His
            1445                1450                1455

Asn Ile Tyr Ser Leu Val Glu Asn Gly Ser Tyr Ile Val Ala Val Asp
            1460                1465                1470

Phe Asp Ser Ile Ser Gly Arg Ile Phe Trp Ser Asp Ala Thr Gln Gly
        1475                1480                1485

Lys Thr Trp Ser Ala Phe Gln Asn Gly Thr Asp Arg Arg Val Val Phe
    1490                1495                1500

Asp Ser Ser Ile Ile Leu Thr Glu Thr Ile Ala Ile Asp Trp Val Gly
1505                1510                1515                1520

Arg Asn Leu Tyr Trp Thr Asp Tyr Ala Leu Glu Thr Ile Glu Val Ser
        1525                1530                1535

Lys Ile Asp Gly Ser His Arg Thr Val Leu Ile Ser Lys Asn Leu Thr
    1540                1545                1550

Asn Pro Arg Gly Leu Ala Leu Asp Pro Arg Met Asn Glu His Leu Leu
    1555                1560                1565
```

```
Phe Trp Ser Asp Trp Gly His His Pro Arg Ile Glu Arg Ala Ser Met
    1570                1575                1580

Asp Gly Ser Met Arg Thr Val Ile Val Gln Asp Lys Ile Phe Trp Pro
1585                1590                1595                1600

Cys Gly Leu Thr Ile Asp Tyr Pro Asn Arg Leu Leu Tyr Phe Met Asp
                1605                1610                1615

Ser Tyr Leu Asp Tyr Met Asp Phe Cys Asp Tyr Asn Gly His His Arg
            1620                1625                1630

Arg Gln Val Ile Ala Ser Asp Leu Ile Ile Arg His Pro Tyr Ala Leu
        1635                1640                1645

Thr Leu Phe Glu Asp Ser Val Tyr Trp Thr Asp Arg Ala Thr Arg Arg
    1650                1655                1660

Val Met Arg Ala Asn Lys Trp His Gly Asn Gln Ser Val Val Met
1665                1670                1675                1680

Tyr Asn Ile Gln Trp Pro Leu Gly Ile Ala Val His Pro Ser Lys
                1685                1690                1695

Gln Pro Asn Ser Val Asn Pro Cys Ala Phe Ser Arg Cys Ser His Leu
            1700                1705                1710

Cys Leu Leu Ser Ser Gln Gly Pro His Phe Tyr Ser Cys Val Cys Pro
        1715                1720                1725

Ser Gly Trp Ser Leu Ser Pro Asp Leu Leu Asn Cys Leu Arg Asp Asp
    1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
                1765                1770                1775

Ile Gln Asn Gly Leu Asp Val Glu Phe Asp Ala Glu Gln Tyr Ile
            1780                1785                1790

Tyr Trp Val Glu Asn Pro Gly Glu Ile His Arg Val Lys Thr Asp Gly
        1795                1800                1805

Thr Asn Arg Thr Val Phe Ala Ser Ile Ser Met Val Gly Pro Ser Met
    1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
                1845                1850                1855

Arg Lys Thr Leu Ile Ala Asn Asp Gly Thr Ala Leu Gly Val Gly Phe
            1860                1865                1870

Pro Ile Gly Ile Thr Val Asp Pro Ala Arg Gly Lys Leu Tyr Trp Ser
        1875                1880                1885

Asp Gln Gly Thr Asp Ser Gly Val Pro Ala Lys Ile Ala Ser Ala Asn
    1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Gln Lys Leu Tyr Trp Ala
                1925                1930                1935

Val Thr Gly Arg Gly Val Ile Glu Arg Gly Asn Val Asp Gly Thr Asp
            1940                1945                1950

Arg Met Ile Leu Val His Gln Leu Ser His Pro Trp Gly Ile Ala Val
        1955                1960                1965

His Asp Ser Phe Leu Tyr Tyr Thr Asp Glu Gln Tyr Glu Val Ile Glu
    1970                1975                1980

Arg Val Asp Lys Ala Thr Gly Ala Asn Lys Ile Val Leu Arg Asp Asn
```

-continued

```
              1985                1990                1995                2000
       Val Pro Asn Leu Arg Gly Leu Gln Val Tyr His Arg Arg Asn Ala Ala
                     2005                2010                2015
       Glu Ser Ser Asn Gly Cys Ser Asn Asn Met Asn Ala Cys Gln Gln Ile
                     2020                2025                2030
       Cys Leu Pro Val Pro Gly Gly Leu Phe Ser Cys Ala Cys Ala Thr Gly
                     2035                2040                2045
       Phe Lys Leu Asn Pro Asp Asn Arg Ser Cys Ser Pro Tyr Asn Ser Phe
                     2050                2055                2060
       Ile Val Val Ser Met Leu Ser Ala Ile Arg Gly Phe Ser Leu Glu Leu
       2065                2070                2075                2080
       Ser Asp His Ser Glu Thr Met Val Pro Val Ala Gly Gln Gly Arg Asn
                     2085                2090                2095
       Ala Leu His Val Asp Val Asp Val Ser Ser Gly Phe Ile Tyr Trp Cys
                     2100                2105                2110
       Asp Phe Ser Ser Ser Val Ala Ser Asp Asn Ala Ile Arg Arg Ile Lys
                     2115                2120                2125
       Pro Asp Gly Ser Ser Leu Met Asn Ile Val Thr His Gly Ile Gly Glu
                     2130                2135                2140
       Asn Gly Val Arg Gly Ile Ala Val Asp Trp Val Ala Gly Asn Leu Tyr
       2145                2150                2155                2160
       Phe Thr Asn Ala Phe Val Ser Glu Thr Leu Ile Glu Val Leu Arg Ile
                     2165                2170                2175
       Asn Thr Thr Tyr Arg Arg Val Leu Leu Lys Val Thr Val Asp Met Pro
                     2180                2185                2190
       Arg His Ile Val Val Asp Pro Lys Asn Arg Tyr Leu Phe Trp Ala Asp
                     2195                2200                2205
       Tyr Gly Gln Arg Pro Lys Ile Glu Arg Ser Phe Leu Asp Cys Thr Asn
                     2210                2215                2220
       Arg Thr Val Leu Val Ser Glu Gly Ile Val Thr Pro Arg Gly Leu Ala
       2225                2230                2235                2240
       Val Asp Arg Ser Asp Gly Tyr Val Tyr Trp Val Asp Asp Ser Leu Asp
                     2245                2250                2255
       Ile Ile Ala Arg Ile Arg Ile Asn Gly Glu Asn Ser Glu Val Ile Arg
                     2260                2265                2270
       Tyr Gly Ser Arg Tyr Pro Thr Pro Tyr Gly Ile Thr Val Phe Glu Asn
                     2275                2280                2285
       Ser Ile Ile Trp Val Asp Arg Asn Leu Lys Lys Ile Phe Gln Ala Ser
                     2290                2295                2300
       Lys Glu Pro Glu Asn Thr Glu Pro Pro Thr Val Ile Arg Asp Asn Ile
       2305                2310                2315                2320
       Asn Trp Leu Arg Asp Val Thr Ile Phe Asp Lys Gln Val Gln Pro Arg
                     2325                2330                2335
       Ser Pro Ala Glu Val Asn Asn Asn Pro Cys Leu Glu Asn Asn Gly Gly
                     2340                2345                2350
       Cys Ser His Leu Cys Phe Ala Leu Pro Gly Leu His Thr Pro Lys Cys
                     2355                2360                2365
       Asp Cys Ala Phe Gly Thr Leu Gln Ser Asp Gly Lys Asn Cys Ala Ile
                     2370                2375                2380
       Ser Thr Glu Asn Phe Leu Ile Phe Ala Leu Ser Asn Ser Leu Arg Ser
       2385                2390                2395                2400
       Leu His Leu Asp Pro Glu Asn His Ser Pro Pro Phe Gln Thr Ile Asn
                     2405                2410                2415
```

```
Val Glu Arg Thr Val Met Ser Leu Asp Tyr Asp Ser Val Ser Asp Arg
         2420                2425                2430

Ile Tyr Phe Thr Gln Asn Leu Ala Ser Gly Val Gly Gln Ile Ser Tyr
         2435                2440                2445

Ala Thr Leu Ser Ser Gly Ile His Thr Pro Thr Val Ile Ala Ser Gly
         2450                2455                2460

Ile Gly Thr Ala Asp Gly Ile Ala Phe Asp Trp Ile Thr Arg Arg Ile
2465                2470                2475                2480

Tyr Tyr Ser Asp Tyr Leu Asn Gln Met Ile Asn Ser Met Ala Glu Asp
             2485                2490                2495

Gly Ser Asn Arg Thr Val Ile Ala Arg Val Pro Lys Pro Arg Ala Ile
         2500                2505                2510

Val Leu Asp Pro Cys Gln Gly Tyr Leu Tyr Trp Ala Asp Trp Asp Thr
         2515                2520                2525

His Ala Lys Ile Glu Arg Ala Thr Leu Gly Gly Asn Phe Arg Val Pro
         2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
         2565                2570                2575

Arg Ser Thr Leu Thr Gly Val Asp Arg Glu Val Ile Val Asn Ala Ala
         2580                2585                2590

Val His Ala Phe Gly Leu Thr Leu Tyr Gly Gln Tyr Ile Tyr Trp Thr
         2595                2600                2605

Asp Leu Tyr Thr Gln Arg Ile Tyr Arg Ala Asn Lys Tyr Asp Gly Ser
         2610                2615                2620

Gly Gln Ile Ala Met Thr Thr Asn Leu Leu Ser Gln Pro Arg Gly Ile
2625                2630                2635                2640

Asn Thr Val Val Lys Asn Gln Lys Gln Gln Cys Asn Asn Pro Cys Glu
         2645                2650                2655

Gln Phe Asn Gly Gly Cys Ser His Ile Cys Ala Pro Gly Pro Asn Gly
         2660                2665                2670

Ala Glu Cys Gln Cys Pro His Glu Gly Asn Trp Tyr Leu Ala Asn Asn
         2675                2680                2685

Arg Lys His Cys Ile Val Asp Asn Gly Glu Arg Cys Gly Ala Ser Ser
         2690                2695                2700

Phe Thr Cys Ser Asn Gly Arg Cys Ile Ser Glu Glu Trp Lys Cys Asp
2705                2710                2715                2720

Asn Asp Asn Asp Cys Gly Asp Gly Ser Asp Glu Met Glu Ser Val Cys
             2725                2730                2735

Ala Leu His Thr Cys Ser Pro Thr Ala Phe Thr Cys Ala Asn Gly Arg
         2740                2745                2750

Cys Val Gln Tyr Ser Tyr Arg Cys Asp Tyr Tyr Asn Asp Cys Gly Asp
         2755                2760                2765

Gly Ser Asp Glu Ala Gly Cys Leu Phe Arg Asp Cys Asn Ala Thr Thr
         2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Asn Thr Ser Asp Glu Lys Asn
         2805                2810                2815

Cys Pro Asp Arg Thr Cys Gln Ser Gly Tyr Thr Lys Cys His Asn Ser
         2820                2825                2830

Asn Ile Cys Ile Pro Arg Val Tyr Leu Cys Asp Gly Asp Asn Asp Cys
         2835                2840                2845
```

```
Gly Asp Asn Ser Asp Glu Asn Pro Thr Tyr Cys Thr Thr His Thr Cys
    2850                2855                2860
Ser Ser Ser Glu Phe Gln Cys Ala Ser Gly Arg Cys Ile Pro Gln His
2865                2870                2875                2880
Trp Tyr Cys Asp Gln Glu Thr Asp Cys Phe Asp Ala Ser Asp Glu Pro
            2885                2890                2895
Ala Ser Cys Gly His Ser Glu Arg Thr Cys Leu Ala Asp Glu Phe Lys
            2900                2905                2910
Cys Asp Gly Gly Arg Cys Ile Pro Ser Glu Trp Ile Cys Asp Gly Asp
            2915                2920                2925
Asn Asp Cys Gly Asp Met Ser Asp Glu Asp Lys Arg His Gln Cys Gln
            2930                2935                2940
Asn Gln Asn Cys Ser Asp Ser Glu Phe Leu Cys Val Asn Asp Arg Pro
2945                2950                2955                2960
Pro Asp Arg Arg Cys Ile Pro Gln Ser Trp Val Cys Asp Gly Asp Val
            2965                2970                2975
Asp Cys Thr Asp Gly Tyr Asp Glu Asn Gln Asn Cys Thr Arg Arg Thr
            2980                2985                2990
Cys Ser Glu Asn Glu Phe Thr Cys Gly Tyr Gly Leu Cys Ile Pro Lys
    2995                3000                3005
Ile Phe Arg Cys Asp Arg His Asn Asp Cys Gly Asp Tyr Ser Asp Glu
    3010                3015                3020
Arg Gly Cys Leu Tyr Gln Thr Cys Gln Gln Asn Gln Phe Thr Cys Gln
3025                3030                3035                3040
Asn Gly Arg Cys Ile Ser Lys Thr Phe Val Cys Asp Glu Asp Asn Asp
            3045                3050                3055
Cys Gly Asp Gly Ser Asp Glu Leu Met His Leu Cys His Thr Pro Glu
            3060                3065                3070
Pro Thr Cys Pro Pro His Glu Phe Lys Cys Asp Asn Gly Arg Cys Ile
    3075                3080                3085
Glu Met Met Lys Leu Cys Asn His Leu Asp Asp Cys Leu Asp Asn Ser
    3090                3095                3100
Asp Glu Lys Gly Cys Gly Ile Asn Glu Cys His Asp Pro Ser Ile Ser
3105                3110                3115                3120
Gly Cys Asp His Asn Cys Thr Asp Thr Leu Thr Ser Phe Tyr Cys Ser
            3125                3130                3135
Cys Arg Pro Gly Tyr Lys Leu Met Ser Asp Lys Arg Thr Cys Val Asp
            3140                3145                3150
Ile Asp Glu Cys Thr Glu Met Pro Phe Val Cys Ser Gln Lys Cys Glu
    3155                3160                3165
Asn Val Ile Gly Ser Tyr Ile Cys Lys Cys Ala Pro Gly Tyr Leu Arg
    3170                3175                3180
Glu Pro Asp Gly Lys Thr Cys Arg Gln Asn Ser Asn Ile Glu Pro Tyr
3185                3190                3195                3200
Leu Ile Phe Ser Asn Arg Tyr Tyr Leu Arg Asn Leu Thr Ile Asp Gly
            3205                3210                3215
Tyr Phe Tyr Ser Leu Ile Leu Glu Gly Leu Asp Asn Val Val Ala Leu
            3220                3225                3230
Asp Phe Asp Arg Val Glu Lys Arg Leu Tyr Trp Ile Asp Thr Gln Arg
            3235                3240                3245
Gln Val Ile Glu Arg Met Phe Leu Asn Lys Thr Asn Lys Glu Thr Ile
    3250                3255                3260
Ile Asn His Arg Leu Pro Ala Ala Glu Ser Leu Ala Val Asp Trp Val
```

```
            3265                3270                3275                3280

Ser Arg Lys Leu Tyr Trp Leu Asp Ala Arg Leu Asp Gly Leu Phe Val
            3285                3290                3295

Ser Asp Leu Asn Gly Gly His Arg Arg Met Leu Ala Gln His Cys Val
            3300                3305                3310

Asp Ala Asn Asn Thr Phe Cys Phe Asp Asn Pro Arg Gly Leu Ala Leu
            3315                3320                3325

His Pro Gln Tyr Gly Tyr Leu Tyr Trp Ala Asp Trp Gly His Arg Ala
            3330                3335                3340

Tyr Ile Gly Arg Val Gly Met Asp Gly Thr Asn Lys Ser Val Ile Ile
3345                3350                3355                3360

Ser Thr Lys Leu Glu Trp Pro Asn Gly Ile Thr Ile Asp Tyr Thr Asn
            3365                3370                3375

Asp Leu Leu Tyr Trp Ala Asp Ala His Leu Gly Tyr Ile Glu Tyr Ser
            3380                3385                3390

Asp Leu Glu Gly His His Arg His Thr Val Tyr Asp Gly Ala Leu Pro
            3395                3400                3405

His Pro Phe Ala Ile Thr Ile Phe Glu Asp Thr Ile Tyr Trp Thr Asp
        3410                3415                3420

Trp Asn Thr Arg Thr Val Glu Lys Gly Asn Lys Tyr Asp Gly Ser Asn
3425                3430                3435                3440

Arg Gln Thr Leu Val Asn Thr Thr His Arg Pro Phe Asp Ile His Val
            3445                3450                3455

Tyr His Pro Tyr Arg Gln Pro Ile Val Ser Asn Pro Cys Gly Thr Asn
            3460                3465                3470

Asn Gly Gly Cys Ser His Leu Cys Leu Ile Lys Pro Gly Gly Lys Gly
        3475                3480                3485

Phe Thr Cys Glu Cys Pro Asp Asp Phe Arg Thr Leu Gln Leu Ser Gly
        3490                3495                3500

Ser Thr Tyr Cys Met Pro Met Cys Ser Ser Thr Gln Phe Leu Cys Ala
3505                3510                3515                3520

Asn Asn Glu Lys Cys Ile Pro Ile Trp Trp Lys Cys Asp Gly Gln Lys
            3525                3530                3535

Asp Cys Ser Asp Gly Ser Asp Glu Leu Ala Leu Cys Pro Gln Arg Phe
            3540                3545                3550

Cys Arg Leu Gly Gln Phe Gln Cys Ser Asp Gly Asn Cys Thr Ser Pro
        3555                3560                3565

Gln Thr Leu Cys Asn Ala His Gln Asn Cys Pro Asp Gly Ser Asp Glu
        3570                3575                3580

Asp Arg Leu Leu Cys Glu Asn His His Cys Asp Ser Asn Glu Trp Gln
3585                3590                3595                3600

Cys Ala Asn Lys Arg Cys Ile Pro Glu Ser Trp Gln Cys Asp Thr Phe
            3605                3610                3615

Asn Asp Cys Glu Asp Asn Ser Asp Glu Asp Ser Ser His Cys Ala Ser
            3620                3625                3630

Arg Thr Cys Arg Pro Gly Gln Phe Arg Cys Ala Asn Gly Arg Cys Ile
        3635                3640                3645

Pro Gln Ala Trp Lys Cys Asp Val Asp Asn Asp Cys Gly Asp His Ser
        3650                3655                3660

Asp Glu Pro Ile Glu Glu Cys Met Ser Ser Ala His Leu Cys Asp Asn
3665                3670                3675                3680

Phe Thr Glu Phe Ser Cys Lys Thr Asn Tyr Arg Cys Ile Pro Lys Trp
            3685                3690                3695
```

```
Ala Val Cys Asn Gly Val Asp Asp Cys Arg Asp Asn Ser Asp Glu Gln
        3700                3705                3710

Gly Cys Glu Glu Arg Thr Cys His Pro Val Gly Asp Phe Arg Cys Lys
        3715                3720                3725

Asn His His Cys Ile Pro Leu Arg Trp Gln Cys Asp Gly Gln Asn Asp
        3730                3735                3740

Cys Gly Asp Asn Ser Asp Glu Glu Asn Cys Ala Pro Arg Glu Cys Thr
3745                3750                3755                3760

Glu Ser Glu Phe Arg Cys Val Asn Gln Gln Cys Ile Pro Ser Arg Trp
                3765                3770                3775

Ile Cys Asp His Tyr Asn Asp Cys Gly Asp Asn Ser Asp Glu Arg Asp
        3780                3785                3790

Cys Glu Met Arg Thr Cys His Pro Glu Tyr Phe Gln Cys Thr Ser Gly
        3795                3800                3805

His Cys Val His Ser Glu Leu Lys Cys Asp Gly Ser Ala Asp Cys Leu
        3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
                3845                3850                3855

Pro Tyr Trp Lys Cys Asp Gly Asp Asp Asp Cys Gly Asp Gly Ser Asp
        3860                3865                3870

Glu Glu Leu His Leu Cys Leu Asp Val Pro Cys Asn Ser Pro Asn Arg
        3875                3880                3885

Phe Arg Cys Asp Asn Asn Arg Cys Ile Tyr Ser His Glu Val Cys Asn
        3890                3895                3900

Gly Val Asp Asp Cys Gly Asp Gly Thr Asp Glu Thr Glu Glu His Cys
3905                3910                3915                3920

Arg Lys Pro Thr Pro Lys Pro Cys Thr Glu Tyr Glu Tyr Lys Cys Gly
                3925                3930                3935

Asn Gly His Cys Ile Pro His Asp Asn Val Cys Asp Asp Ala Asp Asp
        3940                3945                3950

Cys Gly Asp Trp Ser Asp Glu Leu Gly Cys Asn Lys Gly Lys Glu Arg
        3955                3960                3965

Thr Cys Ala Glu Asn Ile Cys Glu Gln Asn Cys Thr Gln Leu Asn Glu
        3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
                4005                4010                4015

Cys Pro Gln His Cys Arg Asn Thr Lys Gly Ser Tyr Glu Cys Val Cys
                4020                4025                4030

Ala Asp Gly Phe Thr Ser Met Ser Asp Arg Pro Gly Lys Arg Cys Ala
        4035                4040                4045

Ala Glu Gly Ser Ser Pro Leu Leu Leu Leu Pro Asp Asn Val Arg Ile
        4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Lys Asp Ile
                4085                4090                4095

Gly Leu Ser Val Val Tyr Tyr Thr Val Arg Gly Glu Gly Ser Arg Phe
                4100                4105                4110

Gly Ala Ile Lys Arg Ala Tyr Ile Pro Asn Phe Glu Ser Gly Arg Asn
        4115                4120                4125
```

```
Asn Leu Val Gln Glu Val Asp Leu Lys Leu Lys Tyr Val Met Gln Pro
    4130                4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
        4165                4170                4175

Lys Trp Leu Ile Ser Thr Asp Leu Asp Gln Pro Ala Ala Ile Ala Val
            4180                4185                4190

Asn Pro Lys Leu Gly Leu Met Phe Trp Thr Asp Trp Gly Lys Glu Pro
    4195                4200                4205

Lys Ile Glu Ser Ala Trp Met Asn Gly Glu Asp Arg Asn Ile Leu Val
4210                4215                4220

Phe Glu Asp Leu Gly Trp Pro Thr Gly Leu Ser Ile Asp Tyr Leu Asn
4225                4230                4235                4240

Asn Asp Arg Ile Tyr Trp Ser Asp Phe Lys Glu Asp Val Ile Glu Thr
        4245                4250                4255

Ile Lys Tyr Asp Gly Thr Asp Arg Arg Val Ile Ala Lys Glu Ala Met
            4260                4265                4270

Asn Pro Tyr Ser Leu Asp Ile Phe Glu Asp Gln Leu Tyr Trp Ile Ser
    4275                4280                4285

Lys Glu Lys Gly Glu Val Trp Lys Gln Asn Lys Phe Gly Gln Gly Lys
4290                4295                4300

Lys Glu Lys Thr Leu Val Val Asn Pro Trp Leu Thr Gln Val Arg Ile
4305                4310                4315                4320

Phe His Gln Leu Arg Tyr Asn Lys Ser Val Pro Asn Leu Cys Lys Gln
        4325                4330                4335

Ile Cys Ser His Leu Cys Leu Leu Arg Pro Gly Gly Tyr Ser Cys Ala
            4340                4345                4350

Cys Pro Gln Gly Ser Ser Phe Ile Glu Gly Ser Thr Thr Glu Cys Asp
    4355                4360                4365

Ala Ala Ile Glu Leu Pro Ile Asn Leu Pro Pro Pro Cys Arg Cys Met
4370                4375                4380

His Gly Gly Asn Cys Tyr Phe Asp Glu Thr Asp Leu Pro Lys Cys Lys
4385                4390                4395                4400

Cys Pro Ser Gly Tyr Thr Gly Lys Tyr Cys Glu Met Ala Phe Ser Lys
        4405                4410                4415

Gly Ile Ser Pro Gly Thr Thr Ala Val Ala Val Leu Leu Thr Ile Leu
            4420                4425                4430

Leu Ile Val Val Ile Gly Ala Leu Ala Ile Ala Gly Phe Phe His Tyr
    4435                4440                4445

Arg Arg Thr Gly Ser Leu Leu Pro Ala Leu Pro Lys Leu Pro Ser Leu
4450                4455                4460

Ser Ser Leu Val Lys Pro Ser Glu Asn Gly Asn Gly Val Thr Phe Arg
4465                4470                4475                4480

Ser Gly Ala Asp Leu Asn Met Asp Ile Gly Val Ser Gly Phe Gly Pro
        4485                4490                4495

Glu Thr Ala Ile Asp Arg Ser Met Ala Met Ser Glu Asp Phe Val Met
            4500                4505                4510

Glu Met Gly Lys Gln Pro Ile Ile Phe Glu Asn Pro Met Tyr Ser Ala
    4515                4520                4525

Arg Asp Ser Ala Val Lys Val Val Gln Pro Ile Gln Val Thr Val Ser
4530                4535                4540

Glu Asn Val Asp Asn Lys Asn Tyr Gly Ser Pro Ile Asn Pro Ser Glu
```

```
                4545                4550                4555                4560

Ile Val Pro Glu Thr Asn Pro Thr Ser Pro Ala Ala Asp Gly Thr Gln
                    4565                4570                4575

Val Thr Lys Trp Asn Leu Phe Lys Arg Lys Ser Lys Gln Thr Thr Asn
                4580                4585                4590

Phe Glu Asn Pro Ile Tyr Ala Gln Met Glu Asn Glu Gln Lys Glu Ser
        4595                4600                4605

Val Ala Ala Thr Pro Pro Pro Ser Pro Ser Leu Pro Ala Lys Pro Lys
    4610                4615                4620

Pro Pro Ser Arg Arg Asp Pro Thr Pro Thr Tyr Ser Ala Thr Glu Asp
4625                4630                4635                4640

Thr Phe Lys Asp Thr Ala Asn Leu Val Lys Glu Asp Ser Glu Val
                4645                4650                4655
```

METHOD FOR MEASURING HUMAN MEGALIN

TECHNICAL FIELD

The present invention relates to a method for measuring human megalin. More particularly, the present invention relates to a method for detecting human megalin comprising quantitatively detecting megalin that is expressed topically and specifically in cells, tissues, and organs where megalin expression is observed in a rapid and simple manner, to thereby enable direct and early diagnosis of the degree to which cells, tissues, and organs are affected and improve and keep from worsening the conditions of disorders and the prognosis via treatment. The present invention can be applied to diagnosis of diseases of organs where megalin expression is observed, such as kidney or lung diseases.

BACKGROUND ART

1. Cloning of Megalin

As a result of a search for an etiologic antigen of Heymann nephritis, which is a model for experimental membranous nephropathy, Kerjaschki, D. and Farquhar, M. G. identified a cell membrane protein, gp330, in 1982 (Kerjaschki D., Farquhar M. G., 1982, Proc. Natl. Acad. Sci. U.S.A., 79, 5557-5561). In 1994, Saito, A. et al. determined the complete primary structure of a rat gp330 and designated it as megalin, because it was the largest cloned cell membrane protein of a vertebrate (Saito A. et al., 1994, Proc. Natl. Acad. Sci. U.S.A., 91, 9725-9729).

2. Megalin-Expressing Site

Megalin is also known as glycoprotein 330 (gp330) or low-density lipoprotein (LDL) receptor-related protein 2 (LRP-2). It is a glycoprotein having a molecular weight of about 600 kDa, which is expressed in kidney proximal tubule epithelial cells, other tissues and cells, such as type II alveolar cells, spermary, uterine endometrium, placenta, or inner ear epithelium, renal epithelium, germo-vitellarium, and neural ectoderm (see Christensen E. I., Willnow, T. E., 1999, J. Am. Soc. Nephrol. 10, 2224-2236; Juhlin C., Klareskog L. et al., 1990, J. Biol. Chem. 265, 8275-8279; and Zheng G, McCluskey R. T. et al., 1994, J. Histochem. Cytochem. 42, 531-542). In the kidney, megalin functions as an endocytosis receptor associated with endocytosis and reabsorption of proteins and the like in the proximal tubule prior to urinary excretion. The reabsorbed proteins and the like are then degraded by lysosomes (see Mausbach A. B., Christensen E. I., 1992, Handbook of Physiology: Renal Physiology, Windhager, editor, New York, Oxford University Press, 42-207).

3. Nucleotide Sequence of Megalin

Megalin is a glycoprotein that is the most frequently expressed on the kidney proximal tubule epithelial membrane of a mammalian animal. The cDNA-encoding sequence thereof has nucleotide identity with the human megalin cDNA sequence having gene accession number U04441 disclosed in Korenberg, J. R. et al. (1994) or the human megalin cDNA sequence having gene accession number U33837 disclosed in Hjaeln, G., et al. (1996) (see Korenberg J. R. et al., 1994, Genomics 22, 88-93; and Hjalm G. et al., 1996, Eur. J. Biochem. 239, 132-137).

Also, rat megalin having homology with human megalin has been discovered by Saito et al. (1994), and the cDNA sequence thereof having gene accession number L34049 has already been disclosed (see Saito A. et al., 1994, Proc. Natl. Acad. Sci. U.S.A., 91, 9725-9729).

4. Amino Acid Sequence and Protein Structure of Megalin

Megalin is a gigantic cell membrane protein consisting of 4,655 amino acids (in the case of human megalin) and 4,660 amino acids (in the case of rat megalin). The molecular weight deduced based on the amino acid sequence is about 520 kDa, and it can be as great as about 600 kDa, when including a sugar chain (see Saito A. et al., 1994, Proc. Natl. Acad. Sci. U.S.A., 91, 9725-9729). Megalin belongs to the LDL receptor gene family, a gigantic extracellular region thereof has four functional domains, and the extracellular region is connected to a thin intracellular region through a single transmembrane region. Megalin is mainly present in a clathrin-coated pit on the glomerulus (rat) or the epithelial luminal membrane (luminal and basal membrane in the glomerular epithelial cell) of the proximal tubule, type II alveolar cell, epididymal glands, thyroid glands, accessory thyroid glands, yolk sac membrane, inner ear, small intestine, or choroidea, and it is associated with intake of various ligands into the cells and metabolism thereof (see Farquhar M. G. et al., 1995, J. Am. Soc. Nephrol. 6, 35-47; and Christensen E. I. et al., 2002, Nat. Rev. Mol. Cell. Biol. 3, 256-266). Low-molecular-weight proteinuria, bone metabolism disorders, respiratory failure, malformation of brain, and other disorders occur in megalin-knockout mice (see Willnow T. E. et al., 1996, Proc. Natl. Acad. Sci. U.S.A., 93, 8460-8464). A megalin homolog is also present in nematodes (*C. elegans*), and the biological importance thereof has been suggested (see Yochem J. et al., 1993, Proc. Natl. Acad. Sci. U.S.A., 90, 4572-4576).

5. Importance of Megalin as a Cause of Nephritis

Megalin, which is a major etiologic antigen of experimental membranous nephropathy (Heymann nephritis), is an epithelial scavenger receptor, and biological and pathological roles thereof have been elucidated. Animal models have been used for a long time in order to elucidate the mechanism of human membranous nephropathy development, and rat Heymann nephritis is a model of membranous nephropathy. The analysis of Heymann nephritis has been more advanced than that of any other model. Saito A. et al. disclosed the results of analysis of the pathological epitope and the ligand-binding domain of Heymann nephritis, and they have also demonstrated the major antigen region of megalin and a functional domain of megalin that mainly contribute to binding to a ligand (see Kerjaschki D. et al., 1992, Proc. Natl. Acad. Sci. U.S.A., 89, 11179-11183; Saito A., Farquhar M. G. et al., 1996, Proc. Natl. Acad. Sci. U.S.A., 93, 8601-8605; Yamazaki H., Farquhar M. G. et al., 1998, J. Am. Soc. Nephrol. 9, 1638-1644; and Orlando R. A., Farquhar M. G. et al., 1997, Proc. Natl. Acad. Sci. U.S.A., 94, 2368-2373).

6. Various Ligands of Megalin

Megalin is expressed most abundantly on the luminal side of the proximal tubule epithelial cells in vivo. In human kidney, megalin expression is not observed at sites other than the proximal tubule epithelial cells, including at glomeruli. Megalin incorporates various ligands (e.g., a low-molecularweight protein or drugs) that are filtered by glomeruli into cells via endocytosis, megalin transports them to lysosomes, and they reappear on the cell surface via recycling (see Farquhar M. G. et al., 1995, J. Am. Soc. Nephrol. 6, 35-47; and Christensen E. I. et al., 2002, Nat. Rev. Mol. Cell. Biol. 3, 256-266). Also, megalin is associated with transcytosis from the luminal side to the basal membrane side. Megalin is also associated with intake and metabolism of binding proteins, such as vitamins A, $B_{12}$, and D (see Christensen E. I. et al., 2002, Nat. Rev. Mol. Cell. Biol. 3, 256-266). Christensen and Willnow demonstrated that megalin mediates reabsorption of three vitamin carrier proteins, vitamin D binding proteins (DBP), retinol binding protein (RBP), and transcobalamin (TC) and vitamins associated therewith; i.e., (OH) vitamin $25D_3$, vitamin A (retinol), and vitamin $B_{12}$ (see Christensen E. I., Willnow T. E., 1999, J. Am. Soc. Nephrol. 10, 2224-2236). Saito A. et al. demonstrated that leptin, which is secreted from adipocytes and increase in the blood of obese patients, is incorporated into and metabolized by the proximal tubule epithelial cells as the megalin ligand (see Saito A., Gejyo F. et al., 2004, Endocrinology. 145, 3935-3940). The adipocytes, that is, accumulated visceral fats, result in combined pathological conditions, i.e., metabolic syndrome. Leptin, which is an adipocytokine secreted from adipocytes, increases in the blood of a metabolic syndrome patient. It is suggested that the kidney is the organ in which leptin in the blood is most likely to accumulate and that leptin plays a nephropathic role (see Tarzi R. M. Lord G. M. et al., 2004, Am. J. Pathol. 164, 385-390). A so-called leptin receptor is also found in a region between the proximal tubule and the collecting tubule located downstream of the megalin functioning region.

The term "metabolic syndrome" is defined as a disease complication of visceral obesity, elevated blood pressure, hyperlipidemia, impaired glucose tolerance, and other symptoms, the primary risk factor of which is insulin resistance. Such conditions are highly likely to lead to development of arteriosclerotic diseases and proteinuria, and may result in the development of nephropathy with glomerulus and renal tubular hypertrophy as histological features. When such a case is combined with apparent diabetes, the feature of hyperglycemia is further developed, diabetic nephropathy is manifested, and the disease conditions may further become serious. Type II diabetes is basically preceded by or simultaneously develops with metabolic syndrome. Accordingly, the feature of nephropathy could be included as nephropathy associated with metabolic syndrome.

Saito A. et al. have conducted an experiment using rat yolk sac epithelium-derived cells (L2 cells) in which megalin is expressed at high levels and found that incorporation of $^{125}$I-labelled AGE (advanced glycation end products) (derived from glucose) into L2 cells would be significantly inhibited by an anti-megalin antibody. Thus, they demonstrated that megalin is associated with a pathway for such incorporation (see Saito A. Gejyo F. et al., 2003, J. Am. Soc. Nephrol. 14, 1123-1131). As a mechanism of diabetic nephropathy development, association of advanced glycation end products (AGE) with glycated and modified proteins by the Maillard reaction has been pointed out. A low-molecular-weight AGE in the blood is filtered by glomeruli, and it is reabsorbed and metabolized by the proximal tubule epithelial cells. If nephropathy further advances, a higher-molecular weight AGE also is filtered by glomeruli, accumulates in the proximal tubule epithelial cells, and imposes excessive metabolic loads. Further, Saito A. et al. also demonstrate that megalin is also associated with incorporation of AGE derived from methylglyoxal, glyceraldehyde, or glycolaldehyde into cells, in addition to glucose. Also, metabolic syndrome is often complicated with hepatopathy, such as fatty liver. Liver type fatty acid binding proteins (L-FABP) that are abundantly present in the liver are released into the blood of a healthy person. In case of hepatopathy, more L-FABP is released into and increased in the blood. Saito A. et al. have also demonstrated that L-FABP in the blood is rapidly filtered by glomeruli and it is reabsorbed by the proximal tubule epithelial cells via megalin (see Takeda T., Gejyo F., Saito A. et al., 2005, Lab. Invest. 85, 522-531).

7. Functional Protein that Interacts with Megalin

In order to elucidate the mechanism of megalin transportation in cells, adaptor molecules that bind to megalin intracellular domains are searched for, and various proteins, such as Dab2, ANKRA, MAGI-1, GAIP, GIPC, Galphai3, MegBP, and ARH, have been identified (see Oleinikov A. V. et al., 2000, Biochem. J. 347, 613-621; Rader K., Farquhar M. G. et al., 2000, J. Am. Soc. Nephrol. 11, 2167-2178; Patrie K. M., Margolis B. et al., 2001, J. Am. Soc. Nephrol. 12, 667-677; Lou X., Farquhar M. G. et al., 2002, J. Am. Soc. Nephrol. 13, 918-927; Petersen H. H., Willnow T. E., 2003, J. Cell. Sci. 116, 453-461; and Takeda T., Farquhar M. G. et al., 2003, Mol. Biol. Cell. 14, 4984-4996). Through such molecules, megalin is associated with endocytosis or transcytosis, and megalin is also associated with signal transmission related thereto. Also, megalin functions conjugatively with a cell membrane receptor, i.e., cubilin, in the proximal tubule epithelial cells, so as to be further involved with incorporation of various ligands into cells (see Saito A. et al., 1994, Proc. Natl. Acad. Sci. U.S.A., 91, 9725-9729). For example, cubilin is a receptor that directly binds to transferrin, albumin, endogenous vitamin $B_{12}$, or the like, and megalin is indirectly involved with endocytosis thereof. Also, megalin is known to interact with the $Na^+$—$H^+$ exchanger isoform 3 (NHE3) in the proximal tubule epithelial cells (see Biemesderfer D. et al., 1999, J. Biol. Chem. 274, 17518-17524). NHE3 is an antiporter that plays an important role in reabsorption of Na+, and NHE3 also influences incorporation of a ligand by megalin (see Hryciw D. H. et al., 2004, Clin. Exp. Pharmacol. Physiol. 31, 372-379). Also, megalin may be involved with inactivation and metabolism of NHE3. At an early stage of diabetic nephropathy or metabolic syndrome-related nephropathy, glomerular filtration becomes excessive. Enhanced reabsorption of Na+ of the proximal tubule is deduced to be a primary cause (see Vallon V. et al., 2003, J. Am. Soc. Nephrol. 14, 530-537), NHE3 plays a key role in such a case, and inactivation and metabolism of MHE3 by megalin is considered to be involved therewith (see Hryciw D. H. et al., 2004, Clin. Exp. Pharmacol. Physiol. 31, 372-379).

8. Correlation of Urinary Excretion of Megalin and Urinary Excretion of Ligand by Megalin Leheste et al. disclosed that megalin-knockout mice and Fanconi syndrome patients with weakened proximal tubule functions would experience increased excretion of proteins and retinol in the urine (see Leheste J. et al., 1999, Am. J. Pathol. 155, 1361-1370). Further, Moestrup S. K. et al. demonstrated that the amount of megalin excreted in urine of patients of Fanconi syndrome is significantly lower than that excreted by healthy individuals. This causes deterioration of megalin functions and expression in the proximal tubule and consequently increases the amount of glomerular-filtered proteins containing retinol-binding proteins excreted in urine (see Anthony G. W., Moestrup S. K. et al., 2002, J. Am. Soc. Nephrol. 13, 125-133).

9. Importance of Megalin Function Found by Experiments Using Models for Uremia and Models for Organ Regeneration As described above, megalin is involved with intake of various low-molecular-weight proteins into the proximal tubule epithelial cells and metabolism thereof. When the pathological condition advances to kidney failure, the mechanism of the metabolism is disturbed, and low-molecular-weight proteins are consequently accumulated in the blood and tissues as uremic proteins. A representative example thereof is $\beta_2$-microglobulin ($\beta_2$-m), which may cause dialysis-related amyloidosis in a long-term dialysis patient (see Gejyo F., Schmid K. et al., 1985, Biochem. Biophys. Res. Commun. 129, 701-706). The aforementioned AGE is also suggested as a cause of arteriosclerosis or organ failure due to its accumulation in the blood of patients with kidney failure or dialysis, and AGE is considered as a type of uremic protein (see Henle T., Miyata T., 2003, Adv. Ren. Replace Ther. 10, 321-331). Further, leptin accumulates in the blood of a dialysis patient and thus is considered to be involved with malnutrition or immunity compromise. Tabata Y. and Gejyo F. et al. disclosed the effects and effectiveness of models for metabolizing uremic protein using megalin functions (see Saito A., Tabata Y., Gejyo F. et al., 2003, J. Am. Soc. Nephrol. 14, 2025-2032 and WO 02/091955). That is, megalin-expressing cells are transplanted as scaffold proteins in vivo, and low-molecular-weight proteins leaked from peripheral blood vessels (newborn blood vessels) are incorporated into the cells with the aid of megalin for metabolization. The megalin-expressing cells used for transplantation (i.e., yolk sac epithelium-derived L2 cells) incorporate and metabolize $\beta_2$-m with the aid of megalin (see Saito A., Tabata Y., Gejyo F. et al., 2003, J. Am. Soc. Nephrol. 14, 2025-2032). Both kidneys of a nude mouse into which L2 cells had been subcutaneously transplanted were removed, the condition of kidney failure was induced, and cell incorporation in the tissue mass into which $^{125}$I-labeled $\beta_2$-m had been transplanted and in organs via intraperitoneal injection was measured. As a result, the cell mass into which L2 cells had been transplanted was found to more significantly incorporate $^{125}$I-labeled $\beta_2$-m compared with other organs, and the $^{125}$I-labeled $\beta_2$-m clearance was found to significantly advance in a group to which L2 cells had been transplanted, compared with a control group into which L2 cells had not been transplanted (see Saito A., Tabata Y., Gejyo F. et al., 2003, J. Am. Soc. Nephrol. 14, 2025-2032).

10. Proteolysis and Urinary Excretion of Megalin

In recent years, the possibility of megalin being subjected to proteolysis in a Notch-like signaling pathway has been suggested (see Zou Z., Biemesderfer D. et al., 2004, J. Biol. Chem. 279, 34302-34310; and Grigorenko A. P. et al., 2004, Proc. Natl. Acad. Sci. U.S.A., 101, 14955-14960). This also includes a two-step cleavage system of shedding of an ectodomain mediated by metalloprotease and intramembrane proteolysis mediated by gamma-secretase.

Also, megalin is known to express in the type II alveolar cell.

Thus, megalin has been extensively studied in respect of its correlation with the metabolism in organs such as the kidney. However, the correlation between diseases of organs, including the kidney, and megalin has not yet been elucidated, and expression of megalin or excretion thereof to the body fluid in connection with a variety of organ diseases has not yet been studied.

To date, a method involving tissue staining or Western blotting using a polyclonal antibody obtained by immunizing an immune animal, such as a rabbit, has been known as a method for detecting megalin.

This technique, however, involves staining of a cell or a protein separated via electrophoresis, and this necessitates very complicated procedures and a long period of time for immobilizing tissues, preparing tissue slices, electrophoresis, and transfer onto the membrane. Thus, it is difficult to quantify megalin.

From the viewpoint of diagnosis of the degrees of functional disorders of tissues or organs, particularly in the case of kidney disorders, there is no effective means for diagnosing kidney tubule failure in a specific and simple manner. At present, many methods of diagnosis that detect albumin, creatinine, $\beta_2$-microglobulin, L-FABP, or the like in urine or blood as a diagnosis marker for renal diseases have been employed. Such diagnosis markers, however, are not derived from kidney tissue, and they merely result from all phenomenon and functions during filtration in kidney glomeruli and reabsorption in kidney tubules. That is, it is difficult to identify glomerulus failure and failure of kidney tubule failure in the kidney even with the use of such marker. Also, such marker is an indirect marker derived from organs other than the kidney. Thus, effectiveness is poor for early diagnosis of a disease. The same applies to KL-6 (markers of acute inflammation), which is an existing diagnosis marker for lung diseases, and particularly for inflammation.

DISCLOSURE OF THE INVENTION

The present invention provides a method for measuring human megalin that can be performed in a simpler manner within a shorter period of time than is possible with conventional techniques, and that can also quantify human megalin. Further, this method enables diagnosis of functional diseases, which are specific to cells, tissues, or organs, in a site-directed manner at an early stage. In particular, the present invention provides a method of measuring megalin levels in urine to detect kidney disorders.

As described above, many reports have been made regarding human megalin, and the correlation thereof with the metabolism of organs such as the kidney or the lung, has been suggested. When organ functions are impaired, however, the way that megalin expression varies and the way that prevalence of megalin changes are unknown.

The present inventors have conducted concentrated studies regarding a method for measuring human megalin with high sensitivity in a rapid manner. Consequently, they discovered a method for accurately measuring megalin in a body fluid sample, such as urine, using a ligand capable of binding to human megalin, and in particular, an anti-human megalin antibody.

Further, the present inventors measured human megalin in the body fluid of a patient with impaired organ functions and discovered that human megalin could be a marker for detecting and diagnosing organ diseases. This has led to the completion of the present invention.

Specifically, the present invention is as follows.

[1] A method for measuring human megalin in a sample using a first ligand capable of binding to human megalin that is bound to a solid support and a second ligand capable of binding to human megalin, the method comprising allowing the sample to react with the first ligand capable of binding to human megalin that is bound to a solid support, allowing the sample to react with the second ligand capable of binding to human megalin, and measuring the second ligand capable of binding to human megalin that is bound to a solid support resulting from formation of a complex of human megalin in the sample and the ligand capable of binding to human megalin.

[2] The method for measuring human megalin in a sample according to [1], which comprises the two steps of the reaction between the first ligand capable of binding to human megalin that is bound to a solid support and the sample and the following reaction between the second ligand capable of binding to human megalin and the sample.

[3] The method for measuring human megalin in a sample according to [1], wherein the reaction between the first ligand capable of binding to human megalin that is bound to a solid support and the sample and the reaction between the second ligand capable of binding to human megalin and the sample are carried out in a single step.

[4] The method for measuring human megalin in a sample according to any of [1] to [3], wherein the first ligand capable of binding to human megalin and the second ligand capable of binding to human megalin are both antibodies.

[5] The method for measuring human megalin in a sample according to any of [1] to [3], wherein the first ligand capable of binding to human megalin is lectin, which is specific to a sugar chain of human megalin, and the second ligand capable of binding to human megalin is an antibody.

[6] The method for measuring human megalin in a sample according to any of [1] to [3], wherein the first ligand capable of binding to human megalin is an antibody and the second ligand capable of binding to human megalin is lectin, which is specific to a sugar chain of human megalin.

[7] The method for measuring human megalin in a sample according to any of [1] to [6], wherein the first ligand capable of binding to human megalin and/or the second ligand capable of binding to human megalin are substances selected from the group consisting of: vitamin-binding protein, which is transcobalamin-vitamin $B_{12}$, vitamin-D-binding protein, or retinol-binding protein; lipoprotein, which is apolipoprotein B, apolipoprotein E, apolipoprotein J/clusterin, or apolipoprotein H; hormone, which is parathyroid hormone (PTH), insulin, epithelial growth factor (EGF), prolactin, leptin, or thyroglobulin, a receptor of any thereof, or a receptor of such hormone; immune or stress response-associated protein, which is immunoglobulin light chain, PAP-1, or $\beta_2$-microglobulin; enzyme, which is PAI-I, PAI-I-urokinase, PAI-I-tPA, prourokinase, lipoprotein lipase, plasminogen, $\alpha$-amylase, $\beta$-amylase, $\alpha_1$-microglobulin, or lysozyme, an inhibitor of any thereof, or an inhibitor of such enzyme; drug or toxin, which is aminoglycoside, polymyxin B, aprotinin, or trichosantin; carrier protein, which is albumin, lactoferrin, hemoglobin, odorant-binding protein, transthyretin, or L-FABP; and receptor-associated protein (RAP), which is cytochrome-c, calcium ($Ca^{2+}$), advanced glycation end products (AGE), cubilin, or $Na^+$—$H^+$ exchanger isoform 3 (NHE3) or binding fragment of such substance.

[8] A method for measuring human megalin in a sample using human megalin or a partial fragment of human megalin that is bound to a solid support and a ligand capable of binding to human megalin, the method comprising allowing the sample to react with the ligand capable of binding to human megalin, allowing the reaction product to react with the human megalin that is bound to a solid support, measuring the ligand capable of binding to human megalin that is bound to a solid support, and competitively quantifying human megalin in the sample based on a decrease in a percentage of the ligand capable of binding to human megalin that is bound to a solid support.

[9] The method for measuring human megalin in a sample according to [8], wherein the ligand capable of binding to human megalin is an anti-human megalin antibody.

[10] A method for measuring human megalin in a sample using a ligand capable of binding to human megalin, the method comprising allowing the sample to react with the ligand capable of binding to human megalin that is bound to a particle to induce agglutination and measuring human megalin based on the degree of resulting agglutination.

[11] The method for measuring human megalin according to [10], wherein the ligand capable of binding to human megalin is an anti-human megalin antibody and the agglutination is immune agglutination.

[12] A method of measuring human megalin by the method according to any of [1] to [11] to detect a disease in an organ in which megalin expression is observed.

[13] The method for detecting a disease in an organ according to [12], wherein the disease in an organ in which megalin expression is observed is a lung disease.

[14] The method for detecting a disease in an organ according to [12], wherein the disease in an organ in which megalin expression is observed is a renal disease.

[15] The method for detecting a renal disease according to [14], wherein the renal disease is renal tubular disorder.

[16] The method according to [14] or [15], wherein the sample is urine.

[17] A kit for detecting a disease in an organ in which megalin expression is observed comprising a ligand capable of binding to human megalin.

[18] The kit for detecting a disease in an organ in which megalin expression is observed according to [17], wherein the ligand capable of binding to human megalin is an anti-human megalin antibody.

[19] The kit for detecting a disease in an organ in which megalin expression is observed according to [18], wherein the disease in an organ in which megalin expression is observed is a lung disease.

[20] The kit for detecting a disease in an organ in which megalin expression is observed according to [18], wherein the disease in an organ in which megalin expression is observed is a renal disease.

[21] The kit for detecting a renal disease according to [20], wherein the renal disease is a renal tubular disorder.

[22] A disease-detecting marker for detecting a disease in an organ in which megalin expression is observed comprising human megalin.

[23] The disease-detecting marker according to [22], wherein the disease in an organ in which megalin expression is observed is a lung disease.

[24] The disease-detecting marker according to [22], wherein the disease in an organ in which megalin expression is observed is a renal disease.

[25] The disease-detecting marker according to [24], wherein the renal disease is a renal tubular disorder.

[26] Use of human megalin as a disease-detecting marker for detecting a disease in an organ in which megalin expression is observed.

[27] The use of human megalin as a disease-detecting marker according to [26], wherein the disease in an organ in which megalin expression is observed is a lung disease.

[28] The use of human megalin as a disease-detecting marker according to [26], wherein the disease in an organ in which megalin expression is observed is a renal disease.

[29] The use of human megalin as a disease-detecting marker according to [28], wherein the renal disease is a renal tubular disorder.

EFFECTS OF THE INVENTION

The method of the present invention enables measurement of human megalin in a sample, such as urine, with high sensitivity and accuracy. When functions of megalin-expressing cells, tissues, or organs are damaged, megalin escapes from the cells and accumulates in a sample. Specifically, measurement of human megalin in a sample enables direct detection and diagnosis of functional disorders of cells, tissues, or organs instead of indirect detection and diagnosis. Accordingly, measurement of human megalin in a sample via the method of the present invention enables detection of a disease in an organ in which megalin expression is observed, such as a renal or lung disease, at an early stage with high accuracy.

This description includes part or all of the contents as disclosed in the description and/or drawings of Japanese Patent Application No. 2006-089306, which is a priority document of the present application.

BEST MODES FOR CARRYING OUT THE INVENTION

Figure 1:
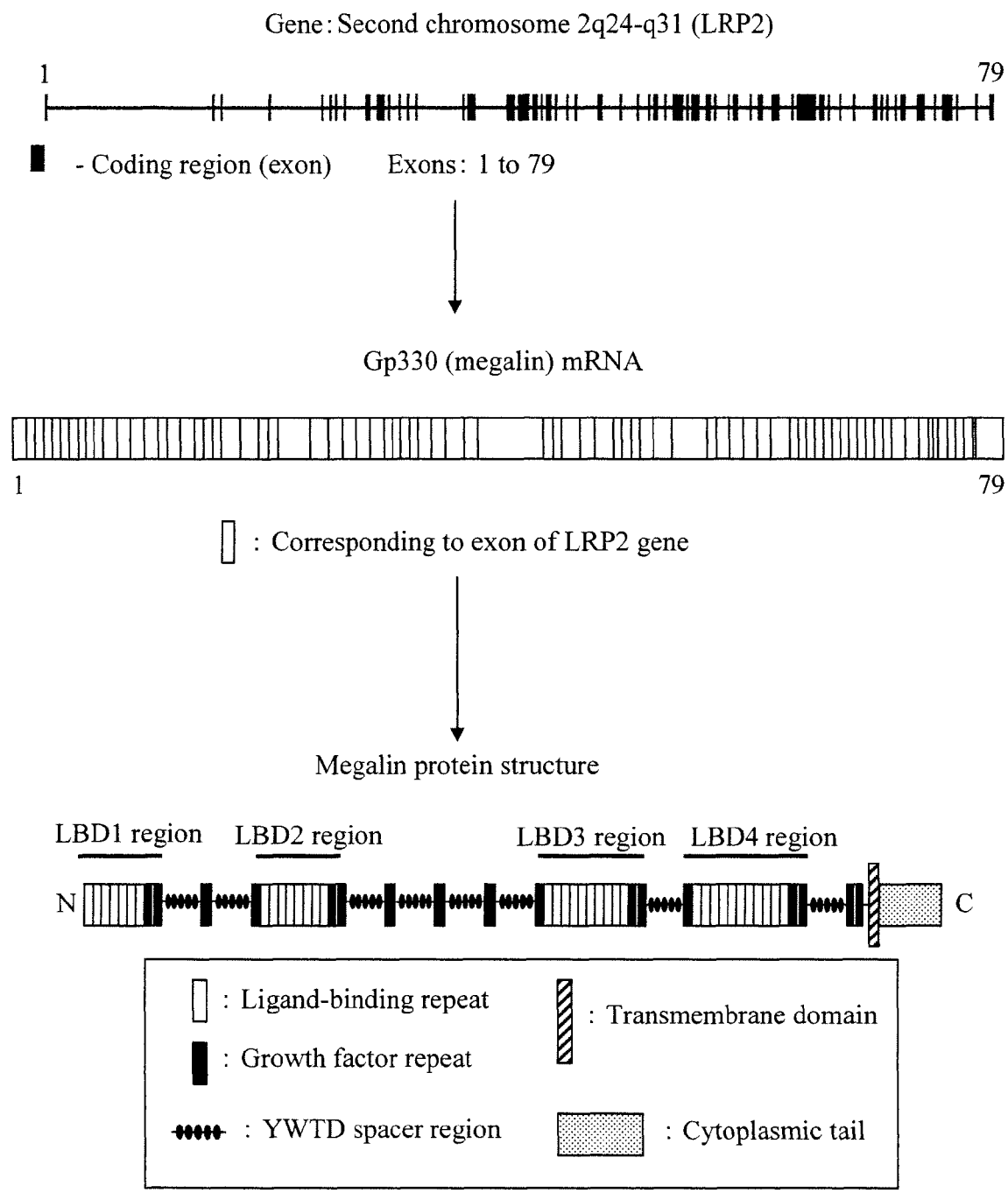
FIG. 1 shows a gene locus and a general protein structure of human megalin.

The present invention concerns a method for measuring human megalin in a sample. SEQ ID NO: 1 shows the nucleotide sequence of human megalin, and SEQ ID NO: 2 shows the amino acid sequence of human megalin.

In the present invention, human megalin is measured using a first ligand capable of binding to human megalin that is bound to a solid support. Any solid support used in conventional immunoanalysis can be used. For example, wells of a plastic microtiter plate or magnetic particles can be preferably used.

An example of a ligand capable of binding to human megalin is an anti-human megalin antibody, and a monoclonal or polyclonal antibody can be used.

Also, lectin that is specific to a sugar chain of human megalin can be used as a ligand capable of binding to human megalin. Examples of lectin include, but are not limited to, concanavalin A, wheat germ lectin (WGA), Ricinus communis lectin (RCA), and lentil lectin (LCA).

Further, examples of a ligand capable of binding to human megalin include substances selected from the group consisting of: vitamin-binding proteins, such as transcobalamin-vitamin $B_{12}$, vitamin-D-binding protein, or retinol-binding protein; lipoproteins, such as apolipoprotein B, apolipoprotein E, apolipoprotein J/clusterin, or apolipoprotein H; hormones, such as parathyroid hormone (PTH), insulin, epithelial growth factor (EGF), prolactin, leptin, or thyroglobulin, a receptor of any thereof, or a receptor of such hormone; immune or stress response-associated proteins, such as immunoglobulin light chain, PAP-1, or $\beta_2$-microglobulin; enzymes, such as PAI-I, PAI-I-urokinase, PAI-I-tPA, prourokinase, lipoprotein lipase, plasminogen, α-amylase, β-amylase, $\alpha_1$-microglobulin, or lysozyme, an inhibitor of any thereof, or an inhibitor of such enzyme; drugs or toxins, such as aminoglycoside, polymyxin B, aprotinin, or trichosantin; carrier proteins, such as albumin, lactoferrin, hemoglobin, odorant-binding protein, transthyretin, or L-FABP; and receptor-associated proteins (RAP), such as cytochrome-c, calcium ($Ca^{2+}$), advanced glycation end products (AGE), cubilin, or $Na^+$—$H^+$ exchanger isoform 3 (NHE3) or binding fragments of such substances. The term "binding fragment" used herein refers to a fragment of the aforementioned substance that includes a site binding to human megalin.

A ligand capable of binding to human megalin, such as an anti-human megalin antibody, can be bound to a solid support by a technique well-known in the art. When a ligand is to be bound to microtiter plate wells, for example, about 3 to 10 µg/ml (preferably about 5 µg/ml) of a solution of a ligand capable of binding to human megalin, such as an antibody, is applied to a solid support and the resultant is then allowed to stand at 4° C. overnight (preferably 12 hours or longer). The recommended density of a solid support mentioned above was theoretically determined when immobilizing a full-length antibody.

The density is determined by theoretical formulae:

$$Q = (2/\sqrt{3}) \cdot (MW/N) \cdot (2r)^{-2} \cdot 10^9 (\text{ng/cm}^2)$$

Q: molecular weight density (ng/cm²)
MW: molecular weight (dalton: Da)
N: Avogadro's number=$6 \cdot 10^{23}$ (mole⁻¹)
r: Stokes radius of molecular=$(R \cdot T_{20})/(6 \cdot \pi \cdot \eta_{20} \cdot D_{20} \cdot N)$ (cm)
R: gas constant=$8.3 \cdot 10^7$ (g·cm²·sec⁻²·° K⁻¹·mole⁻¹)
$T_{20}$: room temperature (20° C.)=293° K
$\eta_{20}$: viscosity of water at 20° C.=$1 \cdot 10^{-2}$ (g·cm⁻¹·sec⁻¹)
$D_{20}$: diff. coeff. of molecular ref. to water at 20° C. (cm²·sec⁻¹)

Such value is applied when immobilizing via physical adsorption. When a ligand capable of binding to human megalin is immobilized, the theoretical density of the relevant solid support is determined, and such density is affected by the aforementioned variation factors, such as individual molecular weight. Thus, the density varies depending on type of individual solid-support molecule, configuration of solid phase, or other conditions. Accordingly, the density is not limited to the aforementioned values. When absorbed on a solid support via covalent binding, also, such density is utilized in the present invention. In such a case, the number of functional groups that are present on the adsorption surface and used for covalent binding is also taken into consideration. The density of a solid support is not limited. After binding, blocking is carried out using bovine serum albumin (hereafter abbreviated to "BSA") or casein, for the purpose of blocking non-specific adsorption sites of a protein, based on a conventional technique. When a solid support is a magnetic bead, the solid support is treated in the same manner as in the case of a microtiter plate.

A ligand capable of binding to human megalin, such as an anti-human megalin antibody, bound to a solid support is allowed to react with a sample, and human megalin in a sample is bound to a solid support with the aid of the ligand capable of binding to human megalin bound to the solid support by a ligand-receptor binding reaction, such as an antigen-antibody reaction. Specifically, a complex of a first ligand capable of binding to human megalin, such as an anti-human megalin antibody, bound to a solid support and human megalin is formed. Any sample may be used, provided that it contains human megalin. Examples of a sample include urine, an alveolar wash, blood, blood serum, blood plasma, and an exhaled air condensate. Such antigen-antibody reaction can be carried out at 4° C. to 45° C., more preferably 20° C. to 40° C., and further preferably 25° C. to 38° C. The duration of the reaction is approximately 10 minutes to 18 hours, more preferably 10 minutes to 1 hour, and further preferably 30 minutes to 1 hour.

After washing, the second ligand capable of binding to human megalin is then allowed to react with the human megalin in a sample bound to a solid support. Specifically, a complex of a first ligand capable of binding to human megalin, such as an anti-human megalin antibody, bound to a solid support, human megalin, and a second ligand capable of binding to human megalin is formed. As the second ligand capable of binding to human megalin, the same substance used as the first ligand capable of binding to human megalin, such as an anti-human megalin antibody, can be used. However, when both the first ligand capable of binding to human megalin and the second ligand capable of binding to human megalin are anti-human megalin monoclonal antibodies, an epitope that is recognized and bound by the first anti-human megalin antibody needs to be different from an epitope that is recognized and bound by the second anti-human megalin antibody. A combination of the first anti-human megalin antibody and the second anti-human megalin antibody can be any combination of a monoclonal antibody and a monoclonal antibody, a monoclonal antibody and a polyclonal antibody, a polyclonal antibody and a monoclonal antibody, and a polyclonal antibody and polyclonal antibody. The reaction can be carried out at 4° C. to 45° C., more preferably 20° C. to 40° C., and further preferably 25° C. to 38° C. The duration of the reaction is about 10 minutes to 18 hours, more preferably 10 minutes to 1 hour, and further preferably 30 minutes to 1 hour. Thus, the second ligand capable of binding to human megalin is bound to a solid support with the aid of human megalin and the first ligand capable of binding to human megalin.

After washing, the second ligand capable of binding to human megalin, such as the second anti-human megalin antibody, bound to a solid support is then measured. This can be carried out via a variety of techniques that are commonly employed in the immunoanalysis field. For example, the second ligand capable of binding to human megalin is labeled with an enzyme, fluorescence, biotin, or radiation label to prepare an enzyme-labeled substance. By assaying such label, the second ligand capable of binding to human megalin bound to a solid support can be measured. Labeling with an enzyme or fluorescence is particularly preferable. Examples of enzyme include peroxidase, alkaline phosphatase, β-galactosidase, and glucose oxidase, and an example of fluorescence is fluorescein isothiocyanate (FITC), although labels are not limited thereto. A label can be detected by allowing a relevant substrate to react with an enzyme-labeled substance and then measuring the resulting dye, fluorescence, emission, or the like. When the second ligand capable of binding to human megalin is not labeled, a labeled third antibody is allowed to react with the second ligand capable of binding to human megalin, and the third antibody can be measured based on such labeling. Thus, the second ligand capable of binding to human megalin can be measured.

A solid support or an anti-human megalin antibody used for labeling may be an immunoglobulin fragment, such as Fab or $F(ab')_2$, specific to human megalin or a recombinant antibody, such as scFv, dsFv, diabody, or minibody, expressed as a recombinant. In the present invention, the term "antibody" also refers to a fragment specific to human megalin. A method for preparing such fragment is well-known in the art.

The aforementioned method comprises the two steps of the reaction between a first ligand capable of binding to human megalin, such as an anti-human megalin antibody, bound to a solid support and a sample, followed by washing, and the reaction of a second ligand capable of binding to human megalin with a sample. Alternatively, a method comprising a single step in which the reaction between a first ligand capable of binding to human megalin, such as an anti-human megalin antibody, bound to a solid support and a sample is carried out simultaneously with the reaction between a second ligand capable of binding to human megalin and a sample.

The present invention further comprises a method for measuring human megalin in a sample using human megalin or a partial fragment of human megalin that is bound to a solid support and a ligand capable of binding to human megalin, the method comprising allowing a sample to react with a ligand capable of binding to human megalin, allowing the reaction product to react with the human megalin that is bound to a solid support, measuring the ligand capable of binding to human megalin that is bound to a solid support, and competitively quantifying human megalin in a sample based on a decrease in a percentage of the ligand capable of binding to human megalin that is bound to a solid support. This method requires binding of human megalin to a solid support, and such binding can be carried out in accordance with the method for binding a substance to a solid support. Also, a partial fragment of human megalin is not limited, and a partial fragment of human megalin to which a ligand capable of binding to human megalin is bound may be used. As a partial fragment of human megalin, a partial sequence of the amino acid sequence of human megalin as shown in SEQ ID NO: 2 can be prepared via chemical synthesis or genetic engineering. The aforementioned ligand capable of binding to human megalin can be used, and an anti-human megalin antibody is particularly preferable. In a competitive method, the amount of human megalin or a partial fragment of human megalin that is bound to a solid support and a ligand capable of binding to human megalin to be used is important. A competitive method is a known technique, and such amount can be adequately determined based on a known technique.

Further, the present invention comprises a method for measuring human megalin using a ligand capable of binding to human megalin, the method comprising allowing a sample to react with a ligand capable of binding to human megalin that is bound to a particle to induce agglutination and measuring human megalin based on the degree of resulting agglutination.

Examples of particles that are used in such method include particles having diameters of 0.05 to 10 μm, preferably latex particles having diameters of 0.1 to 0.4 μm, gelatin particles having diameters of 0.5 to 10 μm, and animal erythrocytes. An antibody can be bound to a particle by a method well-known in the art, such as physical adsorption or covalent binding.

In this method, particles comprising anti-human megalin antibodies bound thereto are mixed with a sample on, for example, a black glass slide, and particles precipitated as a result of agglutination are observed. Thus, human megalin in a sample can be detected. Also, the absorption of the agglutinate may be measured to quantify human megalin. Further, human megalin can also be detected via pulse immunoassay.

The method for measuring human megalin of the present invention enables measurement of not only intact human megalin but also fragments of human megalin.

By measuring human megalin in a sample, whether or not a subject from which a sample has been obtained has disorders in human megalin-expressing cells, tissues, organs, or the like can be evaluated. Specifically, an organ disease or the like can be detected or diagnosed.

Any cells, tissues, or organs may be targets, provided that megalin expression is observed therein. Lung and kidney are preferable, and kidney is further preferable. In case of renal diseases, nephritis or renal tubular disorder can be particularly detected. Also, diabetic nephropathy can be adequately detected. Further, such cells, tissues, or organs can also be used for detecting metabolic syndrome or metabolic syndrome-associated nephropathy.

In the aforementioned subject having functional disorders of cells, tissues, or organs, human megalin escapes from cells and the amount of human megalin in a sample is increased. When human megalin in a sample obtained from the subject is measured in vitro and the concentration of human megalin in a sample is significantly enhanced compared with the concentration of human megalin obtained from a healthy individual, the subject can be diagnosed as having a functional disorder of cells, tissues, or organs.

As described above, urine, an alveolar wash, blood, blood serum, blood plasma, an exhaled air condensate, and the like can be used as samples. When a lung disease is to be detected, use of an alveolar wash is particularly preferable. When a renal disease is to be detected, use of urine is preferable.

Further, measurement of human megalin in a sample obtained from a subject enables evaluation of the risk of being afflicted with functional disorders of cells, tissues, or organs, such as a renal disease. When human megalin in a sample obtained from the subject is measured in vitro and the concentration of human megalin in a sample is significantly enhanced compared with the concentration of human megalin obtained from a healthy individual, the subject can be evaluated as being highly likely to be afflicted with functional disorders of cells, tissues, or organs. That is, measurement of human megalin in a sample enables screening for of subjects who are highly likely to be afflicted with a disease, such as patients-to-be of renal disease, and provision of adequate treatment.

Further, periodical measurement of human megalin in a sample obtained from the subject and monitoring of human megalin concentration enable management of organ functions.

Human megalin can be used as a marker for detecting or diagnosing functional disorders in cells, tissues, or organs where human megalin expression is observed. The present invention comprises use of human megalin as a marker for detecting a functional disorder, i.e., a disease in an organ in which megalin expression is observed. The present invention further comprises a disease-detecting/diagnosing marker for detecting and diagnosing a functional disorder, i.e., a disease in a cell, tissue, or an organ in which megalin expression is observed.

Also, when detecting or diagnosing a functional disorder, i.e., a disease in a cell, tissue, or an organ in which megalin expression is observed, fragments of human megalin may be measured, as well as intact human megalin.

Examples

Hereafter, the present invention is described in greater detail with reference to the examples, although the present invention is not limited to these examples. It should be noted that the method of enzyme-linked immunosorbent assay (ELISA) used in the examples has been heretofore reported by many researchers, since Engvall E. and Perlmann P. made the first report in 1971. There are solid grounds for using this technique (Engvall E, Perlmann P., 1971, Immunochemistry, 8, 871-874).

Hereafter, the present invention is described in greater detail with reference to the examples, although the present invention is not limited to these examples. Detection of human megalin in urine via enzyme-linked immunosorbent assay (ELISA)

(1) Preparation of Mouse Anti-Human Megalin Monoclonal Antibody

A mouse was immunized intraperitoneally with 50 µg of human megalin with an adjuvant several times, and the elevated blood serum titer was confirmed. The spleen was removed 3 days after a booster shot (intravenous immunization), and spleen cells were obtained. The spleen cells were fused with mouse myeloma cells (10:1) in the presence of polyethylene glycol 3500 to prepare hybridoma cells. The resulting cells were cultured for a week in the presence of $CO_2$ at 37° C., and the presence or absence of an anti-human megalin antibody in the culture supernatant was inspected. The cells in the positive wells in which antibody production was observed were diluted via limiting dilution, the resultants were cultured for 2 weeks, and the presence or absence of an anti-human megalin antibody in the culture supernatant was inspected in the same manner. Thereafter, the cells in the positive wells in which antibody production was observed were diluted via limiting dilution, and the resultants were cultured in the same manner. At this stage, cells in which anti-human megalin antibodies have been produced are cultured in a flask, part thereof is suspended in fetal calf serum (FCS) containing 10% dimethyl sulfoxide (DMSO) ($5 \times 10^6$ cells/ml), and the resultant was stored in liquid nitrogen.

Subsequently, supernatants in the wells were used to inspect reactivity of antibodies against human megalin produced in culture supernatants. Human megalin was dissolved in 140 mM NaCl, 2.7 mM KCl, 10 mM $Na_2HPO_4$, and 1.8 mM $KH_2PO_4$ (pH 7.3; hereafter abbreviated as "PBS, pH 7.3"). To wells of a plastic microtiter plate (Nunc-Immuno™Module F8 Maxisorp™ Surface plate, Nalge Nunc International), 100 µl of the solution of human megalin in PBS (pH 7.3) was added per well, and human megalin was then immobilized on the microtiter plate at 3 pmol/well at 4° C. for 12 hours. Thereafter, the solution of human megalin in PBS (pH 7.3) that had been added to the wells was removed via decantation, 145 mM NaCl, 3.6 mM $Na_2HPO_4$, 1.4 mM $KH_2PO_4$, and 0.05% (v./v.) Tween 20 (hereafter abbreviated as "PBS-T") were applied to wells of the microtiter plate at 200 µl/well, PBS-T was removed via decantation, and the excessively adsorbed human megalin in the wells was washed. This process of washing was carried out twice in total. Thereafter, 145 mM NaCl, 7.2 mM $Na_2HPO_4$, 2.8 mM $KH_2PO_4$, 1% (wt./v.) BSA, and 5% (wt./v.) lactose (hereafter abbreviated as a "blocking solution for an antigen-immobilized plate) were applied at 200 µl/well, and insides of the wells of the microtiter plate on which human megalin had been immobilized were blocked at 4° C. for 12 hours. Thereafter, the resultant was stored at 4° C. In order to inspect the reactivity of antibodies in the culture supernatant, the microtiter plate on which human megalin had been immobilized after blocking treatment was used. To wells of the microtiter plate on which human megalin had been immobilized, a hybridoma culture supernatant was added at 100 µl/well, and the plate was heated at 37° C. for 1 hour. Thereafter, the culture supernatant that had been applied to the wells was removed via decantation, PBS-T was applied to the wells of the microtiter plate at 200 µl/well, PBS-T was removed via decantation, and insides of the wells were then washed. This process of washing was carried out three times in total. Thereafter, peroxidase-conjugated goat anti-mouse immunoglobulins (DAKO) were applied to the wells at 100 μl/well (2,000-fold diluted, 0.55 μg/ml), and the resultant was heated at 37° C. for 1 hour. The enzyme-labeled antibody was diluted using 145 mM NaCl, 3.6 mM $Na_2HPO_4$, 1.4 mM $KH_2PO_4$, 0.05% (v./v.) Tween 20, and 0.5% (wt./v.) BSA (hereafter referred to as a "diluent of enzyme-labeled antibody"). Thereafter, the enzyme-labeled antibodies that had been applied to the wells were removed via decantation, PBS-T was applied to the wells of the microtiter plate at 200 μl/well, PBS-T was removed via decantation, and insides of the wells were then washed. This process of washing was carried out three times in total. Thereafter, a 3,3',5,5'-tetramethylbenzidine (hereafter abbreviated as "TMB") solution (TMB One-Step Substrate System: DAKO) was applied to the wells at 100 μl/well as a substrate solution for peroxidase enzyme reaction, and the resultant was allowed to stand at 25° C. for 30 minutes. Immediately thereafter, a 313 mM $H_2SO_4$ solution (hereafter referred to as a "reaction terminator") was applied at 100 μl/well to the substrate solution for reaction in the wells to terminate the enzyme reaction in the wells. Thereafter, the absorption of the wells was measured, and the value obtained by subtracting the absorption at 630 nm from that at 450 nm was designated as an indicator for evaluation of reactivity (Josephy P. D., Mason R. P. et al., 1982, J. Biol. Chem. 257, 3669-3675). Many reports have been heretofore made regarding TMB-based colorimetry since Bos E. S. et al made the first report in 1981, and there are solid grounds for using this technique (Bos E. S. et al., 1981, J. Immunoassay, 2, 187-204).

As a result, monoclonalized hybridoma cells exhibiting strong reactivity of an anti-human megalin antibody to immobilized human megalin were selected, and the class and the subclass of immunoglobulin in the culture supernatant were examined regarding each clone from 100 μl of the stock culture supernatant solution using the mouse immunoglobulin typing kit (Wako Pure Chemical Industries, Ltd.). Based on the results, clones of the IgG class were selected from the resulting monoclone cell library and then the process of ascites preparation was carried out as described below.

Subsequently, these cells were cultured in a 25-ml flask and then in a 75-ml flask. The cells were injected intraperitoneally into a pristane-treated mouse, and ascites was sampled.

(2) Purification of Mouse Anti-Human Megalin Monoclonal (IgG) Antibody

The obtained ascites (10 ml) was mixed with an opacified blood serum-treating agent (FRIGEN (registered trademark) II: Kyowa Pure Chemical Co., Ltd.) at a ratio of 1:1.5 by volume, and the resultant was shaken and stirred for 1 to 2 minutes to delipidize the ascites. The ascites was centrifuged using a centrifuger at 3,000 rpm (1930×g) for 10 minutes, and the centrifuged supernatant of clarified ascites (10 ml) was fractionated. The centrifuged supernatant of ascites (10 ml) was subjected to ammonium sulfate fractionation (final concentration: 50% saturated ammonium sulfate) in an ice bath for 1 hour, and the precipitated immunoglobulin fraction was suspended and dissolved in PBS. This process of ammonium sulfate fractionation was carried out twice in total to obtain a crude immunoglobulin fraction from ascites. The resulting crude immunoglobulin fraction (10 ml) was mixed with an equivalent amount of 20 mM sodium phosphate (pH 7.0; hereafter referred to as "20 mM NaPB (pH 7.0)" and then subjected to affinity purification using a protein G column (HiTrap Protein G HP, 5 ml; Amersham BioSciences)). The sample was adsorbed on a protein G column, 20 mM NaPB (pH 7.0, 50 ml) was flushed through the protein G column, and contaminants other than IgG in the sample were removed by washing. Thereafter, affinity-adsorbed IgG on the protein G column was eluted with 0.1 M glycine-HCl (pH 2.7), and the elution fraction immediately after elution from the column was neutralized with 1M tris(hydroxymethyl)aminomethane-HCl (pH 9.0) and then recovered (hereafter "tris (hydroxymethyl)aminomethane" is abbreviated as "Tris"). After neutralization, the affinity-purified product was dialyzed against PBS in an amount 500 times greater than the purified product by volume at 4° C. for 6 hours, and this process of dialysis was carried out twice in total. The dialysis membrane used for dialysis was a cellulose tube for dialysis (Viskase Companies). The resulting IgG elution fraction was designated as a purified anti-human megalin monoclonal antibody and subjected to storage at 4° C. and procedures described below. The process of purification was performed by connecting the aforementioned protein G column to the BioLogic LP System (Bio Rad Laboratories) at a constant flow rate of 1 ml/min.

(3) Preparation of Microtiter Plate on which Anti-Human Megalin Monoclonal Antibody has been Immobilized The purified anti-human megalin monoclonal antibody was dissolved in PBS (pH 7.3) to result in a final concentration of 5 μg/ml therein. To wells of a plastic microtiter plate (Nunc-Immuno™Module F8 Maxisorp™ Surface plate, Nalge Nunc International), 100 μl of the solution of the anti-human megalin monoclonal antibody in PBS (pH 7.3) was added per well, and the anti-human megalin monoclonal antibody was immobilized on the microtiter plate at 4° C. for 12 hours. Thereafter, the solution of the anti-human megalin monoclonal antibody in PBS (pH 7.3) that had been added to the wells was removed via decantation, PBS-T was added to the wells of the microtiter plate at 200 μl/well, PBS-T was removed via decantation, and the excessively adsorbed anti-human megalin monoclonal antibody in the wells was washed. This process of washing was carried out twice in total. Thereafter, 86 mM NaCl, 100 mM Tris, 0.5% (wt./v.) BSA, and 0.05% (v./v.) Tween 20 (hereafter referred to as a blocking solution for an antibody-immobilized plate) were added at 200 μl/well, and the insides of the wells of the human megalin-immobilized microtiter plate were subjected to blocking at 4° C. for 12 hours. Thereafter, the resultant was stored at 4° C.

(4) Preparation of Peroxidase-Labeled Anti-Human Megalin Monoclonal Antibody

Horseradish peroxidase (hereafter abbreviated as "HRP") (peroxidase from horseradish, Type VI, Sigma) was dissolved in pure water at a concentration of 4 mg/ml, 100 μl of a 100 mM sodium metaperiodate solution was added to 500 μl of the HRP solution (2 mg), and the mixture was agitated at room temperature for 20 minutes. The resultant was dialyzed against a 1 mM sodium acetate (pH 4.0) solution (hereafter referred to as a "1 mM acetate buffer") in an amount 500 times greater than that of the HRP solution by volume at 4° C. for 6 hours, and this procedure was performed twice. The dialysis membrane used for dialysis was a cellulose tube for dialysis (Viskase Companies). Subsequently, the anti-human megalin monoclonal antibody was dissolved in a solution of 2.4 mM $Na_2CO_3$ and 7.6 mM $NaHCO_3$ (pH 9.6) (hereafter referred to as a "10 mM carbonate buffer") at a concentration of 8 mg/ml. A solution of 120 mM $Na_2CO_3$ and 380 mM $NaHCO_3$ (pH 9.6) (hereafter referred to as a "0.5 M carbonate buffer") was added to 500 μl of the HRP solution (2 mg) in an amount one-third thereof by volume, 500 μl of the aforementioned anti-human megalin monoclonal antibody (4 mg) was added thereto, and the resultant was agitated at room temperature for 2 hours. Thereafter, 50 μl of a solution of sodium borohydride (4 mg/ml) was added, and the resultant was agitated in an ice bath for 2 hours. The resultant was subjected to ammonium sulfate fractionation (final concentration: 50% saturated ammonium sulfate) in an ice bath for 1 hour, and the precipitated fraction was suspended and dissolved in 1 ml of a solution of 100 mM Tris, 145 mM NaCl, and 1% (v./v.) BSA (pH 7.6) (hereafter referred to as a "suspension of labeled antibody"). This ammonium sulfate fractionation was carried out twice in total, and a solution of 2.8 mM $KH_2PO_4$, 7.2 mM $Na_2HPO_4$, 145 mM NaCl, 1% (wt./v.) BSA, 0.02% (v./v.) phenol, and 40% (wt./v.) D-sorbitol (hereafter referred to as a labeled-antibody stock solution) was added to the solution of the labeled antibody in an amount three-fourths of the solution of the labeled antibody (hereafter referred to as a labeled-antibody stock solution). The HRP-labeled anti-human megalin monoclonal antibody was obtained. Many reports have been heretofore made regarding the method of HRP labeling, ever since Nakane, P. K. and Kawaoi, A. made the first report in 1974. Thus, there are solid grounds for using this technique (Nakane, P. K., Kawaoi, A., 1974, J. Histochem. Cytochem. 22, 1084).

(5) Measurement of Human Megalin in Urine

Figure 2:
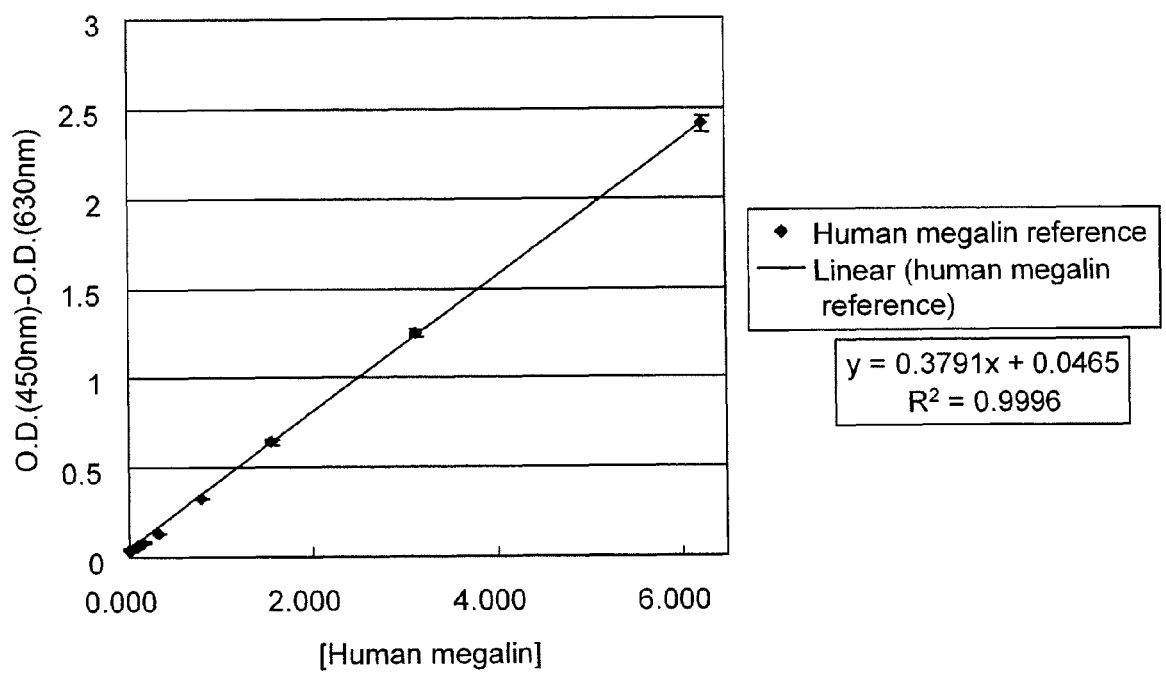
FIG. 2 shows an ELISA calibration curve for detecting human megalin with the use of standard human megalin.
Figure 3:
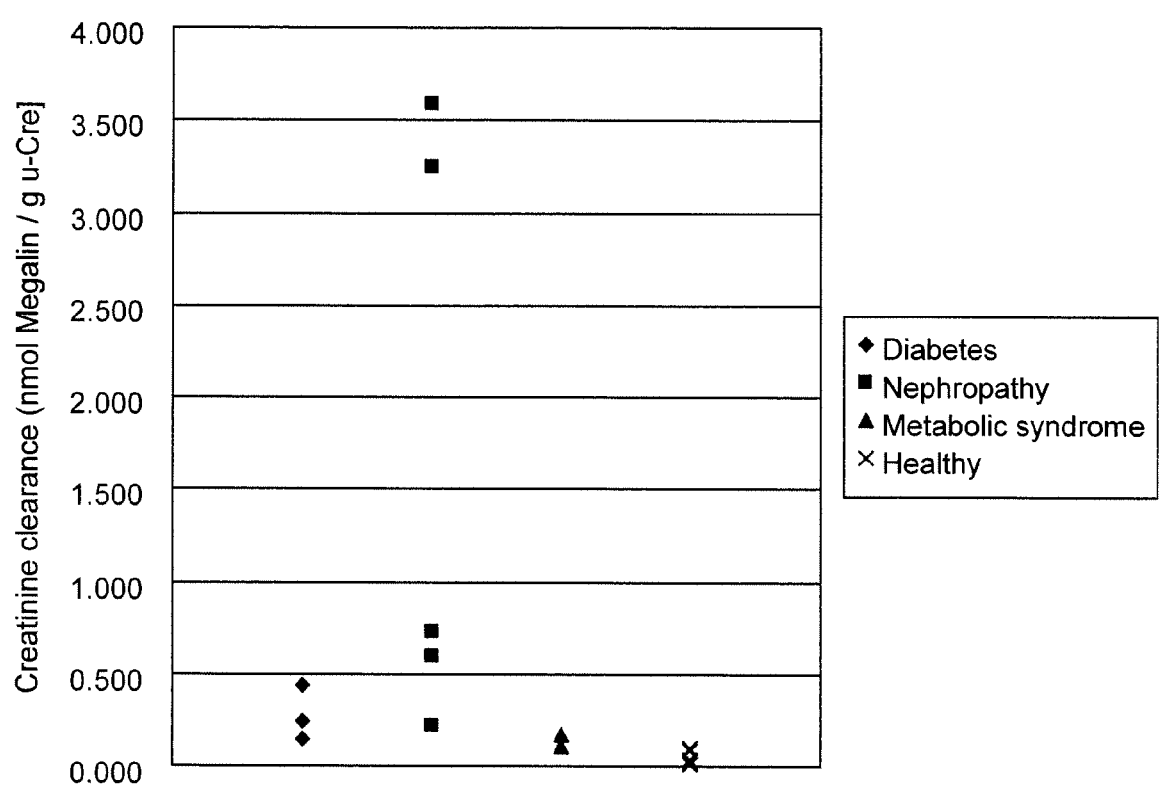
FIG. 3 shows the clinical results of human megalin in urine (part 1).
Figure 4:
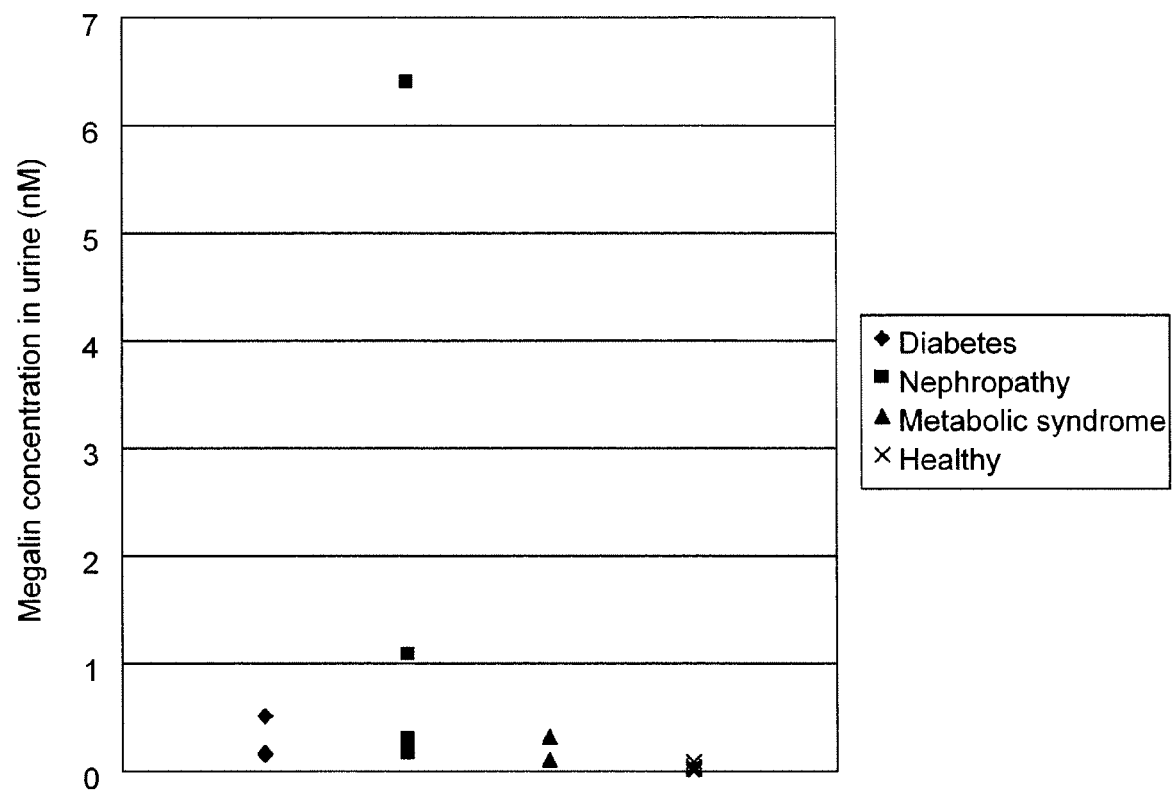
FIG. 4 shows the clinical results of human megalin in urine (part 2).

The aforementioned anti-human megalin monoclonal antibody-immobilized microtiter plate and the HRP-labeled anti-human megalin monoclonal antibody were used to measure human megalin in urine. At the outset, 90 μl of glomerular filtrate was mixed with 10 μl of a solution of 2 M Tris and 0.2 M ethylenediamine-N,N,N',N'-tetraacetic acid (hereafter "ethylenediamine-N,N,N',N'-tetraacetic acid" is abbreviated as EDTA, pH 8.0), and 100 μl of the resulting solution was applied to wells of the microtiter plate to which the anti-human megalin monoclonal antibody has been immobilized. The resultant was allowed to stand at 37° C. for 1 hour, the urine sample solution that had been applied to wells was removed via decantation, PBS-T was applied to wells of the microtiter plate at 200 μl/well, and PBS-T was removed via decantation, followed by washing. The process of washing was carried out three times. Thereafter, the solution of HRP-labeled anti-human megalin monoclonal antibody (the above stock solution was diluted to 10,000-fold with the solution of diluted labeled antibody) was added at 100 μl/well. The resultant was allowed to stand at 37° C. for 1 hour, the solution of HRP-labeled antibody that had been applied to the wells was removed via decantation, PBS-T was added to wells of the microtiter plate at 200 μl/well, and PBS-T was removed via decantation, followed by washing. The process of washing was carried out three times. Subsequently, a TMB solution (TMB One-Step Substrate System; DAKO) was applied to wells as a substrate solution for peroxidase enzyme reaction at 100 μl/well, and the resultant was allowed to stand at 25° C. for 30 minutes. Immediately thereafter, the reaction terminator was added to the substrate solution in the wells at 100 μl/well to terminate the enzyme reaction in the wells. Thereafter, the absorbance of the wells was measured, and the value obtained by subtracting the absorbance at 630 nm from that at 450 nm was designated as an indicator for evaluation of measurement of human megalin in the urine. As the reference sample for the calibration curve, human megalin that was used as an immunological antigen at the time of preparation of an anti-human megalin monoclonal antibody was used, and the results of analysis are shown in Table 1 and FIG. 2. The results of actual clinical measurement of human megalin in the urine are shown in Table 2, FIG. 3, and FIG. 4. As a result, the amount of human megalin excreted to the urine was found to be significantly greater in patients with renal diseases and patient-to-be of renal diseases, compared with healthy individuals (FIGS. 3 and 4). The results of the creatinine clearance tests regarding the amount of megalin excreted to the urine were also similar. This indicates that the concentration at the time of urinary excretion would not matter (FIGS. 3 and 4). The present invention provides a method for measuring human megalin that can be performed in a simpler manner within a shorter period of time than is possible with conventional techniques, and that can also quantify human megalin. Further, this method enables diagnosis of functional diseases that are specific to cells, tissues, or organs, in a site-directed manner at an early stage. The clinical results shown above apparently support such feature of the present invention.

TABLE 1

| [h-megalin] | ELISA calibration curve for detecting human megalin | | | | |
|---|---|---|---|---|---|
| (nM) | n = 1 | n = 2 | n = 3 | AVR. | S.D. |
| 6.250 | 2.4356 | 2.4416 | 2.3576 | 2.4116 | 0.0469 |
| 3.125 | 1.2551 | 1.2596 | 1.2261 | 1.2469 | 0.0182 |
| 1.563 | 0.6288 | 0.6576 | 0.6358 | 0.6407 | 0.0150 |
| 0.781 | 0.3282 | 0.3296 | 0.3282 | 0.3287 | 0.0008 |
| 0.313 | 0.1341 | 0.1359 | 0.1370 | 0.1357 | 0.0015 |
| 0.156 | 0.0788 | 0.0917 | 0.0858 | 0.0854 | 0.0065 |
| 0.078 | 0.0582 | 0.0638 | 0.0727 | 0.0649 | 0.0073 |
| 0.031 | 0.0390 | 0.0503 | 0.0468 | 0.0454 | 0.0058 |
| 0.000 | 0.0465 | 0.0409 | 0.0431 | 0.0435 | 0.0028 |

TABLE 2

| Item | | Creatinine in urine Enzyme method: | Megalin in urine ELISA | | |
|---|---|---|---|---|---|
| Method of measurement | | Color method | | | Creatinine clearance |
| Background of samples | Sample No. | [u-Cre] (mg/dl) | O.D. (450 nm) – O.D. (630 nm) | [Megalin] (nM) | (nmol megalin/g Cre) |
| Diabetes | D-1 | 117.96 | 0.241 | 0.513 | 0.435 |
|  | D-2 | 68.16 | 0.110 | 0.168 | 0.246 |
|  | D-3 | 102.53 | 0.102 | 0.146 | 0.142 |
| Nephropathy | N-1 | 178.52 | 2.472 | 6.398 | 3.584 |
|  | N-2 | 33.55 | 0.459 | 1.088 | 3.243 |
|  | N-3 | 41.24 | 0.161 | 0.302 | 0.732 |
|  | N-4 | 78.29 | 0.110 | 0.168 | 0.215 |
|  | N-5 | 36.97 | 0.129 | 0.218 | 0.590 |
| Metabolic syndrome | M-1 | 302.32 | 0.169 | 0.323 | 0.107 |
|  | M-2 | 59.56 | 0.086 | 0.104 | 0.175 |
| Healthy individuals | H-1 | 44.11 | 0.061 | 0.038 | 0.086 |
|  | H-2 | 92.72 | 0.082 | 0.094 | 0.101 |

TABLE 2-continued

| | Creatinine in urine Enzyme method: | Megalin in urine ELISA | | |
|---|---|---|---|---|
| Method of measurement | Color method | | | Creatinine clearance |
| Background of samples | Sample No. | [u-Cre] (mg/dl) | O.D. (450 nm) – O.D. (630 nm) | [Megalin] (nM) | (nmol megalin/g Cre) |
| | H-3 | 134.72 | 0.056 | 0.025 | 0.019 |
| | H-4 | 123.59 | 0.063 | 0.044 | 0.036 |
| | H-5 | 104.31 | 0.052 | 0.015 | 0.014 |
| | H-6 | 96.64 | 0.050 | 0.009 | 0.009 |

All publications, patents, and patent applications cited herein are incorporated herein by reference in their entirety.

The invention claimed is:

1. A method for detecting a renal disease in which megalin expression is observed by measuring human megalin in a urine sample, comprising:
   (i) allowing the sample to react with a first ligand that is capable of binding to human megalin and that is bound to a solid support,
   (ii) allowing the sample to react with the second ligand, wherein the second ligand is capable of binding to human megalin, and then
   (iii) measuring the level of human megalin in the sample by measuring the amount of the complex formed between the first ligand, the human megalin and the second ligand, wherein an increased level of human megalin indicates a renal disease that is selected from the group consisting of nephritis, tubular renal disorder, and nephropathy.

2. The method according to claim wherein step (i) and step (ii) are carried out sequentially.

3. The method according to claim 1, wherein step (i) and step (ii) are carried out concurrently.

4. The method according to claim 1, wherein the first ligand and the second ligand are both antibodies.

5. The method according to claim 1, wherein the first ligand is lectin, which is specific to a sugar chain of human megalin, and the second ligand is an antibody.

6. The method according to claim 1, wherein the first ligand is an antibody and the second ligand is lectin, which is specific to a sugar chain of human megalin.

7. The method according to claim 1, wherein the first ligand is selected from the group consisting of: vitamin-binding protein, which is transcobalamin-vitamin $B_{12}$, vitamin-D-binding protein, or retinol-binding protein; lipoprotein, which is apolipoprotein B, apolipoprotein E, apolipoprotein J/clusterin, or apolipoprotein H; hormone, which is parathyroid hormone (PTH), insulin, epithelial growth factor (EGF), prolactin, leptin, or thyroglobulin, a receptor of any thereof, or a receptor of such hormone; immune or stress response-associated protein, which is immunoglobulin light chain, purple acid phosphatase 1 (PAP-1), or $\beta_2$-microglobulin; enzyme, which is plasminogen activator inhibitor-I (PAI-I), plasminogen activator inhibitor-I-urokinase (PAI-I-urokinase), plasminogen activator inhibitor-I-tissue plasminogen activator (PAI-I-tPA), prourokinase, lipoprotein lipase, plasminogen, α-amylase, β-amylase, $\alpha_1$-microglobulin, or lysozyme, an inhibitor of any thereof, or an inhibitor of such enzyme; drug or toxin, which is aminoglycoside, polymyxin aprotinin, or trichosantin; carrier protein, which is albumin, lactoferrin, hemoglobin, odorant-binding protein, transthyretin, or liver type fatty acid binding proteins (L-FABP); and receptor-associated protein (RAP), which is cytochrome-c, calcium ($Ca^{2+}$), advanced glycation end products (AGE), cubilin, or $Na^+$—$H^+$ exchanger isoform 3 (NHE3) or binding fragment of such substance, and the second ligand is an antibody.

8. The method according to claim 1, wherein the first ligand is an antibody and the second ligand is selected from the group consisting of vitamin-binding protein, which is transcobalamin-vitamin $B_{12}$, vitamin-D-binding protein, or retinol-binding protein; lipoprotein, which is apolipoprotein B, apolipoprotein E, apolipoprotein J/clusterin, or apolipoprotein H; hormone, which is parathyroid hormone (PTH), insulin, epithelial growth factor (EGF), prolactin, leptin, or thyroglobulin, a receptor of any thereof, or a receptor of such hormone; immune or stress response-associated protein, which is immunoglobulin light chain, purple acid phosphatase 1 (PAP-1), or $\beta_2$-microglobulin; enzyme, which is plasminogen activator inhibitor-I (PAI-I), plasminogen activator inhibitor-I-urokinase (PAI-I-urokinase), plasminogen activator inhibitor-I-tissue plasminogen activator (PAI-I-tPA), prourokinase, lipoprotein lipase, plasminogen, α-amylase, β-amylase, $\alpha_1$-microglobulin, or lysozyme, an inhibitor of any thereof, or an inhibitor of such enzyme; drug or toxin, which is aminoglycoside, polymyxin B, aprotinin, or trichosantin; carrier protein, which is albumin, lactoferrin, hemoglobin, odorant-binding protein, transthyretin, or liver type fatty acid binding proteins (L-FABP); and receptor-associated protein (RAP), which is cytochrome-c, calcium ($Ca^{2+}$), advanced glycation end products (AGE), cubilin, or $Na^+$—$H^+$ exchanger isoform 3 (NHE3) or binding fragment of such substance.

9. The method according to claim 1, wherein said renal disease is nephritis.

10. The method according to claim 1, wherein said renal disease is nephropathy.

11. The method according to claim 1, wherein said renal disease is renal tubular disorder.

* * * * *